United States Patent
Davies et al.

(10) Patent No.: US 12,399,963 B2
(45) Date of Patent: Aug. 26, 2025

(54) SYSTEM AND METHOD FOR CONFIGURABLE MULTI-FACTOR HEALTH CREDENTIAL VALIDATION

(71) Applicant: Salesforce, Inc., San Francisco, CA (US)

(72) Inventors: Alan Davies, San Francisco, CA (US); Shawn Butterfield, Pitt Meadows (CA); Sai Lakshminaraayana, San Francisco, CA (US); Ganbaatar Arslanbaatar, Mountain View, CA (US); Kevin Lun, Redmond, WA (US); Jianwu Zhao, Redmond, WA (US)

(73) Assignee: Salesforce, Inc., San Francisco, CA (US)

( * ) Notice: Subject to any disclaimer, the term of this patent is extended or adjusted under 35 U.S.C. 154(b) by 364 days.

(21) Appl. No.: 18/056,705

(22) Filed: Nov. 17, 2022

(65) Prior Publication Data
US 2024/0169036 A1    May 23, 2024

(51) Int. Cl.
G06F 21/31 (2013.01)
G16H 10/20 (2018.01)
G16H 10/60 (2018.01)

(52) U.S. Cl.
CPC .............. *G06F 21/31* (2013.01); *G16H 10/20* (2018.01); *G16H 10/60* (2018.01)

(58) Field of Classification Search
CPC ......... G06F 21/31; G16H 10/20; G16H 10/60
See application file for complete search history.

(56) References Cited

U.S. PATENT DOCUMENTS

| | | | |
|---|---|---|---|
| 8,225,271 B2* | 7/2012 | Eldridge | G05B 19/0426 717/109 |
| 10,949,074 B2* | 3/2021 | Nelson | G06F 3/0482 |
| 11,868,505 B2 | 1/2024 | Shu et al. | |
| 2018/0219810 A1* | 8/2018 | Santos Ramirez | G06Q 10/107 |
| 2020/0265070 A1* | 8/2020 | Rapaport | G06Q 10/10 |
| 2021/0303569 A1* | 9/2021 | Morganstern | G06F 16/24535 |
| 2022/0269801 A1 | 8/2022 | Hua et al. | |
| 2023/0196471 A1* | 6/2023 | Mendell | G06Q 40/08 705/4 |
| 2024/0005432 A1* | 1/2024 | Aman | G16H 10/40 |

* cited by examiner

*Primary Examiner* — Sm A Rahman
(74) *Attorney, Agent, or Firm* — Nicholson De Vos Webster & Elliott LLP

(57) ABSTRACT

System and method for managing health and safety protocols for occasions, including validation of health verification requirements, asynchronous communication, and generation of multi-factor health credentials. All components of the system can be configured within an integrated graphical user interface (GUI). These components, or subsystems, include a health verification subsystem to indicate one or more health verification requirements for attending the occasion, an occasion communication subsystem to manage communication with prospective visitors to the occasion, and an occasion access subsystem to generate electronic passes to the occasion for prospective visitors who comply with the health verification requirements. Health information provided by a prospective visitor is verified, a visitor/occasion specific QR code is generated and sent to the visitor in an email message. The configuration data to define the operation of the various subsystems is stored in accordance with a flexible and portable data schema comprising a plurality of interrelated objects.

19 Claims, 15 Drawing Sheets

SYSTEM AND METHOD FOR CONFIGURABLE MULTI-FACTOR HEALTH CREDENTIAL VALIDATION

TECHNICAL FIELD

One or more implementations relate to the field of computer systems for providing health tracking and verification services; and more specifically, to a system and method for configuring, issuing, and validating multi-factor health credentials.

BACKGROUND ART

Recent data shows that getting people together safely and in-person is imperative to building and maintaining culture, employee retention, satisfaction, and business growth. At the same time, businesses struggle to manage testing, health and entry protocols to ensure safe in-person experiences at events and in the workplace. These difficulties arise from both the continually changing rules and recommendations from local and state government agencies and the lack of a scalable and configurable platform to manage the health status of employees. As such, a robust and scalable platform is needed for managing health information such as employee testing and vaccination status.

BRIEF DESCRIPTION OF THE DRAWINGS

The following figures use like reference numbers to refer to like elements. Although the following figures depict various example implementations, alternative implementations are within the spirit and scope of the appended claims. In the drawings:

FIGS. 7A-G illustrate various examples of an admin GUI for configuring health verification requirements for access to an occasion;

DETAILED DESCRIPTION

Figure 1A:
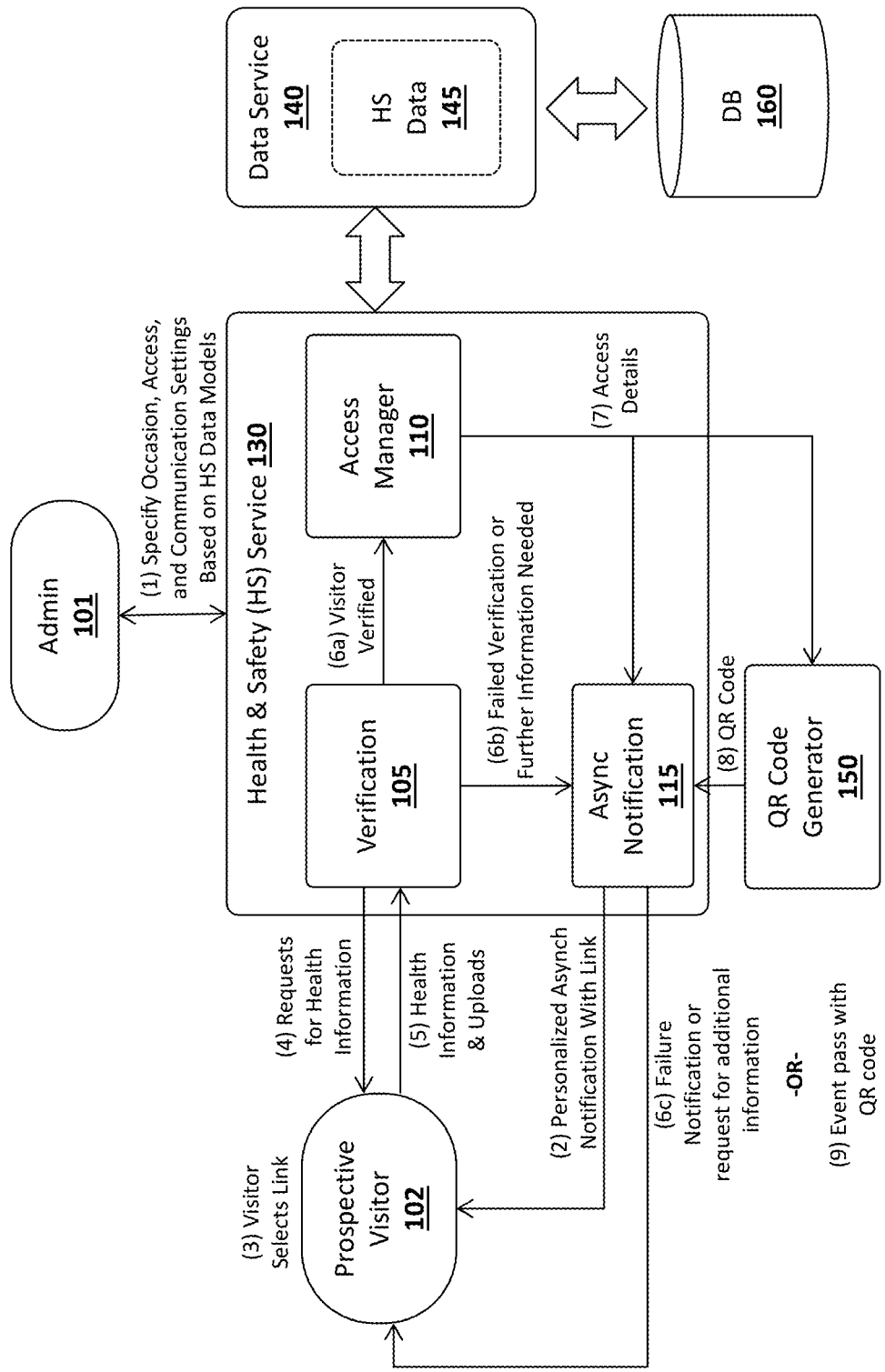
FIG. 1A illustrates one implementation of a process and functional architecture for performing health verifications for an occasion.

The following description includes implementations of a system and method for configuration and validation of multi-factor health credentials. These implementations can be used, for example, by organizations such as businesses, governmental entities, event venues, and community groups to manage testing and health status verification capabilities and protocols, while automating and streamlining entry into events and workplaces with secure credentials.

In particular, implementations of the invention include a flexible, robust platform and associated protocols to bring people back together safely, in accordance with evolving health and safety protocols (such as those related to Covid-19). These protocols may include (but are not limited to) testing and vaccine status requirements, identity and registration, and personalized communication as public health guidelines change. For example, using the implementations described below, a business hosting a large-scale customer event can define and automate testing protocols, including personalized messaging to attendees related to testing requirements and deadlines, to identify positive test result cases prior to the event.

The implementations described below streamline testing and health status reporting with agility and securely manage testing and vaccination results across one platform. For example, if first responders test positive for Covid-19 through an integrated testing platform, they no longer need to visit a physical location to verify their Covid-19 health status in-person to get approval for paid leave. Their test results are automatically loaded into the platform, enabling improved tracking for the availability of other critical workers to ensure adequate staffing is in place in the face of rising Covid-19 rates.

Certain implementations described here automate workplace entry and combine identification and health status into a single, secure, multifactor pass for validated access. These implementations may provide seamless integration with existing health certificates such as SMART Health Cards and EU Digital COVID Certificates, allowing customers to standardize and automate vaccine verification and testing in place of the antiquated, manual verification process. For example, a human resources (HR) team focused on getting its employees and contractors back to the workplace safely can use these implementations to automate entry into a building with a secure digital pass once a negative test result is detected.

The terms "event" and "occasion" are used synonymously herein to refer to a gathering of two or more individuals at a specified time and the terms "visitor" and "prospective visitor" are used synonymously to refer to an individual who may attend the event (e.g., an individual who is invited to the event and can attend only after providing health verifications as described herein). In some implementations, different visitor types may be defined to differentiate between those individuals attending the event or "attendees", and those individuals participating in the event or "participants."

The implementations described below may be used to validate health information and control admission to any form of event or occasion including a formally announced event scheduled at a particular venue (e.g., a sporting event, fundraiser, conference, wedding, etc) or simply a return to the workplace for employees of a business (e.g., following a holiday or vacation). In some of these implementations, events are configured as occasion records. Each occasion has its own rules, regulations, communications, and layouts, which are configurable for each occasion using a common data schema.

Health verification implementations on current systems rely on a multitude of static templates—one for each type of verification. Moreover, each of these templates requires a plurality of sub-templates for different scenarios (e.g., when an initial submission based on a primary template is rejected, and a follow-up submission is needed). The implementations described below address these limitations with a flexible data object schema and associated user interface features for integrating and modifying health verification requests.

FIG. 1A illustrates one implementation in which a health and safety (HS) service 130 coordinates requests for health information and verification of health information prior to an event. As described below, the HS service 130 is designed for configurability and is highly flexible to address the screening requirements of different occasions with different groups of prospective visitors 102. The HS data 145 used by the HS service 130 when performing its functions (e.g., visitor data, occasion data, communication data, etc) is accessed from a database 160 via a data service 140. For example, the HS service 130 may use an API exposed by the data service 140 to read, modify, and write the HS data 145. In some implementations described below, an efficient and scalable data model and schema is used to store and manage the HS data 145.

Based on the particular event and the number of prospective visitors 102, an administrator 101 (e.g., a user permitted to make configuration changes within the HS service 130) specifies settings for a new occasion, including health requirements, access settings, communication settings, and a list of prospective visitors (transaction (1)). Both the administrator 101 and prospective visitors 102 shown in FIG. 1A represent client devices operated by the administrator 101 and prospective visitors, where the client devices execute the software as described herein for rendering graphical user interfaces (GUIs) for entering and submitting data to the HS service 130. As described below, the occasion settings may be specified within an admin GUI organized based on the data model and schema of the underlying HS data 145. The administrator may select various options in accordance with the data model based on the type of new occasion being scheduled. In some instances, the HS service 130 provides the administrator 101 with a set of pre-configured templates or forms constructed under the HS data model for common types of events or prior events.

Once the new occasion has been configured and executed by the administrator 101, asynchronous notification logic 115 generates personalized asynchronous notifications to each of the prospective visitors 102 (transaction (2)). For example, the communication settings, as stored in the HS data 145, may indicate a particular format and content for email requests which the asynchronous notification logic 115 uses to dynamically generate the email messages. In one embodiment, the administrator 101 configures static and dynamic fields to be included in the header, body, and/or footer of each email message. The static fields include the basic message text and graphics associated with the email such as a greeting, representative graphics, and instructions indicating requirements to attend the event. The dynamic fields represent visitor-specific or occasion-specific data which the asynchronous notification logic 115 inserts into each email message. For example, the asynchronous notification logic 115 may replace one or more dynamic fields with the visitor's name, email address, and a visitor-specific link which the prospective visitor selects to provide the requested health information.

In some implementations, all or a portion of the asynchronous notification logic 115 is implemented on a separate service, which communicates with the HS service 130 via an API. Once example of an asynchronous notification service 160 is described below with respect to FIG. 2. In some instances, the HS service 130 constructs the asynchronous messages, and merely provides the constructed asynchronous messages for transmission by the asynchronous notification service 115. In any case, asynchronous messages such as email messages are constructed based on the communication configuration specified in the HS data 145 for the given occasion, and may include personalized verbiage describing the purpose of the email message and one or more links directing the prospective visitor 102 to a health verification form.

In some implementations, when a prospective visitor 102 selects the link in the body of the email message (transaction (3)), the visitor is directed to verification logic 105 on the HS service 130 which requests the health information required for the event (transaction (4)). For example, the verification logic 105 may provide a web page, form, or other type of data entry object with a questionnaire to be answered by the prospective visitor 102. By way of example, and not limitation, the questionnaire may ask whether the prospective visitor is experiencing any flu-like symptoms and/or has any other physical ailments; whether the visitor has tested positive for Covid-19 (and the relevant dates); and whether the visitor has been in physical contact for the last 10 days with anyone who has tested positive. Yes/No selection boxes may be provided in which the prospective visitor can provide answers, as well as a "completed" button to select when all questions have been answered. Other implementations may obviously include a different, potentially more detailed set of questions, depending on the requirements of the occasion and the particular health concerns.

In one implementation, after the prospective visitor completes the questionnaire, the verification logic 105 determines whether any of the answers disqualify the prospective visitor 102 from attendance at the event. If not, then the verification logic 105 may initiate further actions such as providing a link to upload health documentation (e.g., a negative test result, vaccination status, etc). Alternatively, this link may be provided within the questionnaire itself.

If the verification logic 105 determines that one or more of the prospective visitor's responses raise a health concern or disqualify the prospective visitor from attending the event, then the verification logic 105 notifies the asynchronous notification logic 150 (transaction (6b)), which sends a new email to the prospective visitor 102, either informing the prospective visitor 102 of the reasons why a pass to attend the event is not being granted or requesting additional information related to the visitor's health (transaction (6c)). In the latter case, the asynchronous notification logic 115 may dynamically generate a second email with a link to connect the prospective visitor 102 to the verification logic 105 to provide the additional information.

If the answers on the questionnaire and documentation provided by the prospective visitor meet the health verification requirements, then the verification logic notifies an access manager 110 that the prospective visitor has been verified for attendance at the event. In response, the access manager 110 provides access details (transaction (7)) based on the access settings specified by the administrator 101. By way of example, and not limitation, the access manager a particular duration of time may be specified or a particular date range may be set, after which the prospective visitor is required to provide an updated health status. In some implementations, the access manager 110 generates a QR code via QR code generator 150 which the prospective visitor can use to gain entrance to the occasion.

Additional information may be included in the access details such as a particular level of access based on the identity of the prospective visitor (e.g., attendee vs participant) and/or the current number of visitors registered for the event or portions of the event (e.g., the visitor may only have the option to attend certain portions based on registration numbers for other portions). The access details provided by the access manager 110 may include a combination of visitor-specific data and occasion-specific data. For example, in some implementations, access details includes a combination of a unique Visitor ID and the Occasion ID; however, various other combinations of data may be used.

The QR code generator 150 uses the access details to generate the visitor-specific QR code to be scanned at the event. In one implementation, the QR code is provided to asynchronous notification logic 115 (transaction (8)) which generates an asynchronous message (e.g., an email message) containing the QR code or a link to the QR code and transmits the message to the prospective visitor (transaction (9)) (e.g., using communication settings data specified in the HS data 145). The prospective visitor then uses the QR code to access the event for the duration of time specified by the corresponding access settings. While email messages are described above to implement asynchronous communication, various other messaging formats may be used including text messaging and instant messaging.

In some implementations, the QR code generator 150 is managed in a separate service, such as the authentication service 250 described below with respect to FIG. 2. In these implementations, the HS service 130 communicates with other services via an API (e.g., passing messages in accordance with the specified API).

Figure 1B:
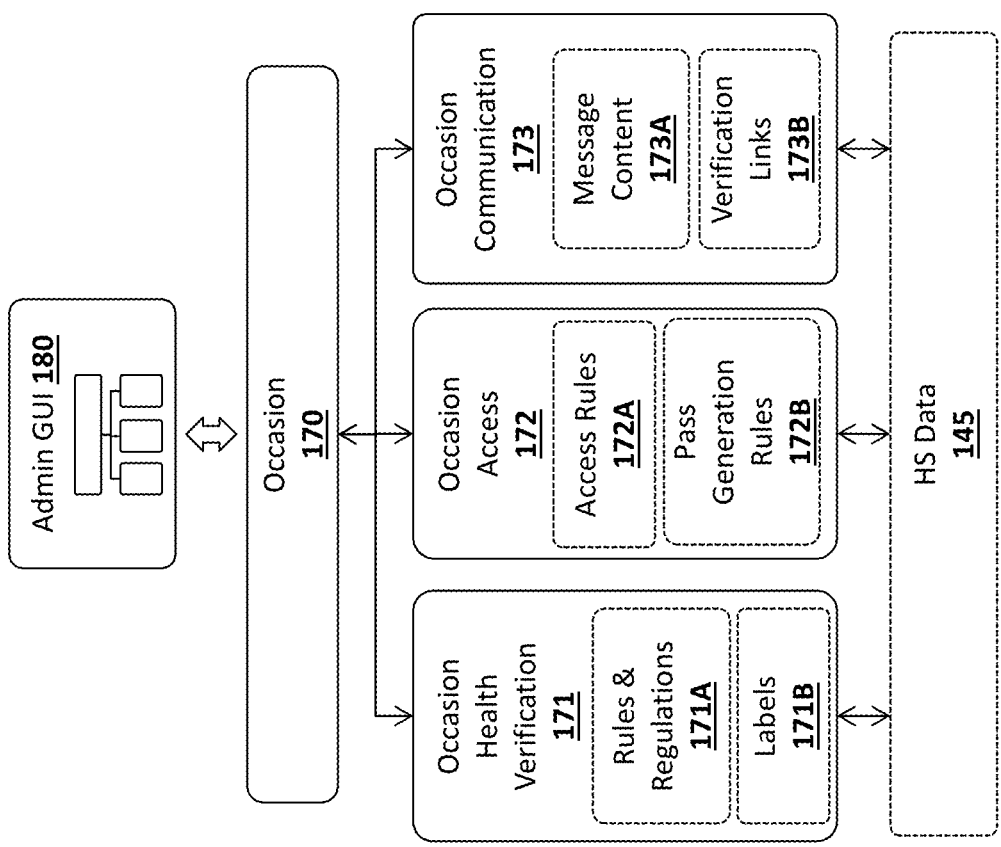
FIG. 1B illustrates one implementation of an architecture for health verifications.

As illustrated in FIG. 1B, some implementations include a set of discrete, separately-configurable subsystems 171-173 which operate together to perform the health verification, communications, and access management operations described herein for an occasion 170. An occasion health verification subsystem 171 performs health verifications based on a set of rules and regulations 171A and labels 171B specified by an administrator via an admin GUI 180. The labels 171B comprise selectable and configurable elements for specifying text, graphics, links and dynamic fields to be included in the header, footer, and body of the asynchronously transmitted messages. The currently operative set of rules and regulations 171A indicate the particular set of health verification requirements for attendance to the current occasion 170. In some implementations, the admin GUI 180 generates editable configuration forms based on the data model/schema of the HS data 145, allowing the administrator to configure new rules and regulations or to modify existing rules and regulations for the occasion 180—which can then be installed or plugged in to the occasion health verification subsystem 171. Different combinations of rules and regulations 171A objects may be selected for the occasion 170, such as rules and regulations object for vaccine requirements and another rules and regulations object for testing requirements.

By way of example, and not limitation, the rules and regulations 171A may indicate a required vaccine status for prospective visitors, including acceptable vaccine types and the timing associated with vaccination. The rules and regulations 171A may also specify testing requirements for attending the occasion, such as the maximum number of days prior to the occasion that the test can be performed, and the types of tests which are accepted. As new information becomes available regarding health recommendations, and new vaccines and tests become available, these may be added to the operative rules and regulations 171A for a given occasion 170 from within the admin GUI 180.

An occasion access subsystem 172 manages access privileges to the occasion 170 based on information provided by the occasion health verification subsystem 171. For example, when a prospective visitor has submitted health information which meets the requirements of the currently operative rules and regulations 171A for the occasion 170, the occasion health verification subsystem 171 sends a request to the occasion access subsystem 172 to grant access to the prospective visitor. The occasion access subsystem 172 generates an occasion pass based on pass generation rules 172B, e.g., causing a QR code to be generated as described above. The occasion access subsystem 172 operates in accordance with a set of access rules 172A which, like the rules and regulations 171A, are configurable by the administrator via the admin GUI 180. For example, the access rules may specify a particular duration of time for which the health verification is valid and/or may specify a particular level of access to the occasion (e.g., based on the identity of the prospective visitor, based on whether the prospective visitor is an attendee of the occasion or a participant in the occasion, etc).

An occasion communication subsystem 173 manages all communication with prospective visitors based on the operations performed by the occasion health verification subsystem 171 and the occasion access subsystem 172. An administrator may use the admin GUI 180 to specify different message content 173A and/or verification links 173B to be included in messages sent at different stages in the process. As mentioned, the message content 173A may be configured with different sets of configurable labels 171B within the occasion health verification subsystem 171, specifying text, graphics, links and dynamic fields to be included in the header, footer, and body of the email messages. Once a particular type of email message is configured via the labels 171B, the underlying message content 173A is stored as three separate files: one for each of the header, footer, and body. These files may be provided to the occasion communication subsystem 173 when dynamically generating personalized email messages for a current type of email. Some implementations of the Admin GUI 180 provides fields for identifying the header, body, and footer files when configuring email communication settings. By way of example, and not limitation, the header and footer may include graphics and/or text associated with the event, while the substance of each message and verification links may be included in the message body.

Thus, once the rules and regulations 171A and labels 171B are configured for the occasion 170, a request is transmitted to the occasion communication subsystem 173 to send the initial email messages requesting health information, including the message content 173A and verification links 173B dynamically generated from the header, footer, and body files.

When a prospective visitor has submitted the required health information, and this information is verified, the occasion health verification subsystem 171, sends a request to the occasion access subsystem 172 to generate a pass to the occasion 170 for the prospective visitor (e.g., via a QR code or other form of identification) and transmits a request to the occasion communication subsystem 173 to send a verification email using a different set of files for the header, footer, and body. The email message includes the pass generated by the occasion access subsystem 172. In this example, the occasion communication subsystem 173 may request the pass from the occasion access subsystem 172 and embed the corresponding QR code in the email message body (e.g., using a link to the occasion access subsystem provided in the email message body).

If the prospective visitor submits health verification information which is insufficient for access to the event (e.g., submitting a test result outside of the minimum number of days, indicating flu-like symptoms on the questionnaire, etc), then the occasion health verification subsystem 171 sends a request to the occasion communication subsystem 173 to send a different type of email message, as defined by another set of header, footer, and body files. The occasion communication subsystem 173 then generates the notification email, in accordance with message content 173A based (on the email body file) indicating the reason(s) why the prospective visitor is not verified to attend the occasion 170 and/or a different link 173B for the prospective visitor to provide additional health information, if applicable.

The described subsystems 171-173 and integrated admin GUI 180 for making configuration changes provide a high level of flexibility, allowing an administrator to precisely configure health verification requirements for different types of occasions 170 and as new health recommendations are released—without impacting other portions of the system. Because the subsystems 171-173 operate separately and/or independently, changes can be made to one subsystem without impacting the others.

Figure 2:
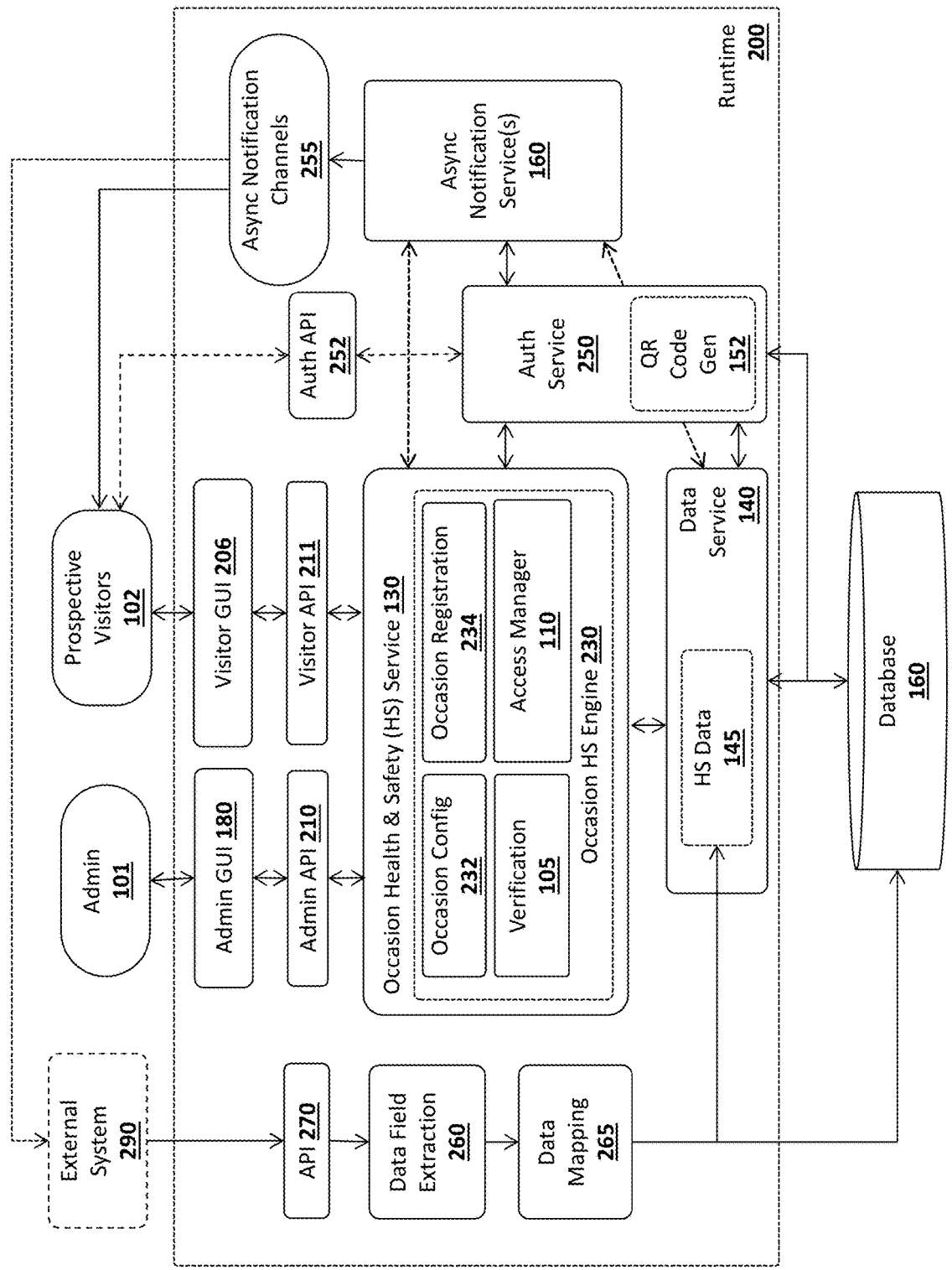
FIG. 2 illustrates a runtime and associated services in accordance with at least one implementation.

FIG. 2 illustrates additional details of certain implementations including the HS service 130, an authentication service 250, and the asynchronous notification service 160 operating within a common runtime environment 200. An admin GUI 180 and a visitor GUI 206 are provided for the administrator 101 and prospective visitors 102, respectively. The GUIs, 205 and 206, transmit requests and receive responses from the HS service 130 via an admin API 210 and visitor API 211, respectively. In these implementations, the admin API 210 supports the functions required by the administrator 101 to configure the HS service 130 for different occasions, as described herein, while the visitor API 211 supports functions for requesting and receiving health information from prospective visitors 102. For example, when a prospective visitor selects the link in the email request generated by the asynchronous notification service 160, the questionnaire and request for documentation may be provided through the visitor API 211 and GUI 206.

A health & safety (HS) engine 230 is executed within the HS service 130 to perform the operations specified in the occasion configuration, and to manage occasion registration 234 for the group of prospective visitors associated with the occasion. While this discussion will focus on a single occasion configuration 232 and a single occasion registration 234, multiple instances of the occasion configuration and occasion registration data may be processed in parallel for multiple occasions.

The occasion configuration 232 is interpreted by the verification logic 105 to determine the verification operations to perform for the occasion. For example, the occasion configuration 232 may require collecting the health information and health authentication documents for prospective visitors to the occasion and coordinating the communication mechanisms to be used for notifying and requesting data from prospective visitors. The access manager 110 interprets the occasion configuration 232 to determine the scope of access provided to each prospective visitor, including the duration of access before new health information is required and the start and end date/time of the event.

The occasion registration 234 tracks the list of prospective visitors currently registered for the event and the status of each prospective visitor. The visitor status may include, for example, visitors who have met the health requirements of the occasion, the effective date and time of each visitor's health information (e.g., the date/time of a negative test), visitors who have both met the health requirements and registered for the event, visitors who have been denied attendance, visitors who have not responded, and visitors for whom additional information is required and/or has been requested. The access manager 110 interprets the visitor status information from the occasion registration 234 when generating a pass for each visitor for a specified duration (e.g., when requesting generation of a QR code).

In some implementation, the verification logic 105 periodically queries the occasion registration 234 to identify any visitor passes which are nearing expiration (e.g., within 48 hours, 24 hours, etc). For these visitors, the verification logic 105 may generate a new message in accordance with the occasion configuration 232 requesting a supplemental verification. As previously described, the message may include a link to upload a new negative test result and/or to respond to a supplemental questionnaire. The asynchronous notification service 160 then transmits these messages to the group of prospective visitors over asynchronous notification channels 255. The asynchronous messages may be email messages as described above, but may also include text messages (e.g., SMS messages), various forms of instant messages (e.g., such Google chat or Microsoft Teams), and/or application-specific asynchronous notifications provided on (e.g., such as Apple notifications generated for installed apps).

In the implementation shown in FIG. 2, an authentication service 250 securely manages the operation of the QR generator 152 to ensure that QR codes are only generated for successfully authenticated entities (e.g., other services). In these implementations, the HS engine 230 establishes a secure communication channel with the authentication service 250 prior to sending requests for QR codes on behalf of prospective visitors. For implementations which require enhanced security, the authentication service 250 may directly request authentication by prospective visitors 102 (as indicated by the dotted arrow between the authentication service 250 and prospective visitors 102). In these instances, once a prospective visitor 102 has complied with the health requirements for the occasion (e.g., uploading requested test results, etc), the prospective visitor is redirected to the authentication service 250 which performs authentication operations to verify the identify of the prospective visitor. Various forms of user authentication may be performed including password-based authentication, biometric authentication, and/or transmission of a one-time password to the visitor's email address or phone number. The specific authentication techniques may be based on the information known about the visitor. For example, if the authentication service 250 has access to the prospective visitor's employee records (e.g., stored in the database 160), then it may prompt the visitor to enter private information stored in those records (e.g., the visitor's social security number, passport number, home phone number, etc). However, if the only information available is the prospective visitor's cell number and/or email address, then the authentication service 250 may send a one-time passcode over one of these asynchronous communication channels 255 via the asynchronous notification service 160 and prompt the prospective visitor to provide the passcode for authentication. In some instances, the prospective visitor 102 enters the passcode via the visitor API 211 which the HS service 130 securely provides to the authentication service 250. In other implementations, the prospective visitor uses a browser or app to connect directly to the authentication service 250 via an authentication API 252.

Once the prospective visitor 102 is successfully authenticated, the authentication service 250 instructs the QR code generator 152 to generate the prospective visitor's QR code 152, which is included in the asynchronous message sent by the asynchronous notification service 160 over an asynchronous notification channel 255 (e.g., an email message as previously described).

The data used to generate the QR code is stored in the occasion registration 234 for the prospective visitor. When the visitor arrives at the occasion, a QR code scanner at the occasion/event location captures the QR code. The data from the QR code is compared against the occasion registration data 234 and the user is provided with access to the occasion if there is a match. If not, then the user is denied access. The occasion registration data 234 may be stored at a storage repository local to the occasion to improve performance.

In some implementations, a list of prospective visitors who are to be invited to attend the event is bulk-downloaded from an external system 290 via an API 270 and converted into the HS data 145, so that it can be accessed by the HS service 130 when performing the operations described herein. In many cases, the data format used by the external system 290 may be different than the data model/schema of the HS data 145. As such, in one implementation, data field extraction logic 260 extracts the data fields associated with each visitor and data mapping logic 265 maps the data into the data model/schema of the HS data 145. In some implementations, the data is provided as a JSON stream which is parsed by the data field extraction logic 260 to extract the relevant fields for each visitor, which is stored in an intermediate metadata format. The data mapping logic 265 then maps the data fields stored in the intermediate metadata format to the HS data 145 schema/model.

Figure 3:
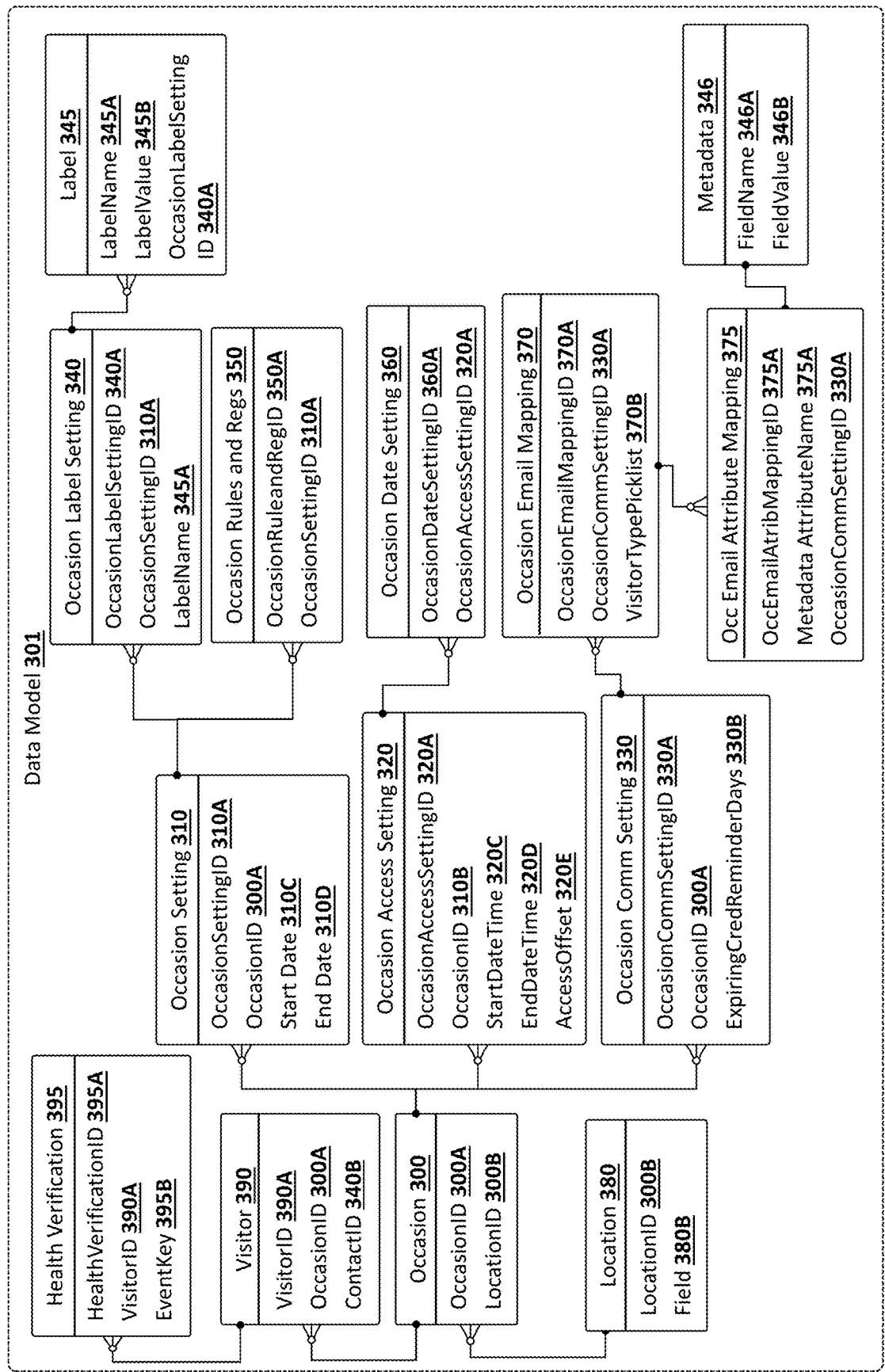
FIG. 3 illustrates a portion of a data model implemented in one or more implementations.

FIG. 3 illustrates an example of a data model 301 comprising an object representation for organizing the HS data 145 used by the some implementations of the HS service 130. Note that the data model 301 is merely one particular example in one implementation; the underlying principles of the invention are not limited to any specific arrangement of data or user interface elements.

In FIG. 3, an Occasion object 300 includes an Occasion ID 300A to uniquely identify the occasion and a Location ID 300B to associate it with a Location object 380 identifying the location associated with the occasion (e.g., an event venue, a workplace, etc). The Location object 380 includes a Location ID 300B for unique identification of the location and one or more fields 380B to provide additional location information. The Occasion object 300 is associated with a plurality of Visitor objects 390 representing visitors invited to the occasion, each of which includes a Visitor ID 390A to uniquely identify the visitor, the Occasion ID 300A to associate the visitor with the occasion, and a Contact ID 340B which may be used to retrieve additional contact information associated with the visitor.

Note that the Occasion object 300 itself does not include significant data and primarily serves the purpose of a parent object or wrapper for the various child objects which provide the underlying configuration data for the occasion. In particular, the Occasion object 300 is associated with one or more Occasion Setting objects 310, Occasion Access Setting objects 320, and Occasion Communication Setting objects 330. This arrangement provides significant flexibility for associating different occasion settings, access settings, and communication settings with each occasion, without requiring a modification to the base Occasion object 300 itself. Thus, as health verification and testing requirements change, occasion, access, and communication settings may be modified and automatically associated with occasions.

The Occasion Setting object 310 contains the data of a verification form and the rules for how a health verification is created. It includes an Occasion Setting ID 310A comprising a unique identifier for the current occasion settings and an Occasion ID 300A associating the occasion setting with the Occasion 300. A start date 310B and end date 310C are also included indicating the starting and ending dates for the current occasion, respectively. Alternatively, or in addition, the start and end dates may be indicated under the Occasion Access Setting object 320.

The Occasion Setting object 310 may be associated with one or more Occasion Label Setting objects 340 and an Occasion Rules and Regulations object 350, such that the settings for each occasion may be specified using different sets of labels (e.g., static and dynamic text fields) and rules/regulations. Moreover, labels and rules/regulations may be added, modified, or deleted, without affecting the base Occasion Setting object 310.

The illustrated Occasion Label Setting includes an Occasion Label Setting ID 340A to uniquely identify the associated label, the Occasion Setting ID 310A to associate the label with the Occasion Setting object 310. The Occasion Rules and Regulations object 350 includes an Occasion Rule and Reg ID 350A to uniquely identify the associated rule/regulation, the Occasion Setting ID 310A to associate the rule/regulation with the Occasion Setting object 310, and one or more Label Name 350B values to identify one or more Labels 345 associated with the rule/regulation.

A plurality of labels may be configured under the occasion label settings to construct the various asynchronous notification messages described herein including the initial email message and all subsequent email messages sent to prospective visitors. By way of example, and not limitation, the initial email message sent to a visitor may include a label specifying the visitor's language (e.g., English, Spanish, German, etc), another label comprising the text for the welcome title (e.g., "Welcome Back to the Office"), one or more labels comprising text explaining the health requirements for the occasion, and a field for dynamically entering the user's name to personalize the message. One or more labels may also provide the links described above to connect the Visitor with the HS service 130 (e.g., to respond to the questionnaire and/or upload health testing documentation).

Similarly, one or more instances of an Occasion Rules and Regs object 350 may be associated with the Occasion Setting object 310. The illustrated Occasion Rules and Regs object 350 includes a unique Occasion Rule and Reg ID 350A for identification and the Occasion Setting ID 310A to associate it with the Occasion Setting 310. Each Occasion rules and Regs object 350 may specify requirements for entrance to the occasion (indicated by Occasion object 300). By way of example, and not limitation, a first rule/regulation (specified via an instance of Occasion Rule and Regs object 350) may indicate the vaccine verification requirements including a list of approved vaccine types, one or more verification methods (e.g., documentation upload, visitor affirmation, etc) and the number of days before the event that the vaccine must have been administered. A second rule/regulation object may indicate the health test upload requirements including a listing of approved test types and the maximum number of days prior to the event that the test must be performed.

These Rules and Regulations objects 350 may be updated by the administrator 101, for example, as new information becomes available regarding the efficacy and timing associated with different types of vaccines and testing techniques. Significantly, these individual objects can be individually updated to change the current set of rules/regulations without requiring changes to any other object instances within the data model 301.

FIG. 3 also illustrates Occasion Access Settings Object 320 which includes an Occasion Access Setting ID 320A for identification, the Occasion ID 310B to associate it with the occasion, a Start Date/Time value 320C, an End Date/Time value 320D, and an Access Offset value 320E. In some implementations, the Access Offset value 320E indicates a period of time from the date/time of the visitor's negative test result during which the visitor is permitted to attend the occasion. Towards the end of this time period, the verification logic 105 or access manager 110 may generate an email to notify the visitor (as described above). The Start Date/Time value 320C and End Date/Time value 320D specify the start date/time and end date/time of a period when the visitor is permitted to attend the event without further health validation.

An Occasion Date Setting object 360 provides information related to the occasion date(s) and includes an Occasion Date Setting ID 360A for identification and an Occasion Access Setting ID 320A to associate it with the Occasion Access Setting object 320.

In various implementations, the data contained in the Occasion Access Settings object 320 is encoded in the QR code generated for a visitor once that visitor has complied with the verification requirements.

An Occasion Communication Setting object 330 specifies parameters for communication with prospective visitors 102 and includes an Occasion Communication Setting object 330, an Occasion ID 300A to associate it with the Occasion 300, and an Expiring Credential Reminder Days 330B to indicate the number of days before expiration of a visitor's credentials to send a reminder to the visitor. The Occasion Communication Setting object 330 may be associated with multiple Occasion Email Mapping objects 370, which include an Occasion Email Mapping ID for identification, Occasion Communication Setting ID 330A to associate it with the Occasion Communication Setting object 330. One or more Occasion Email Attribute Mapping objects 375 are associated with each Occasion Email Mapping object 370 to provide visitor data needed for the email notifications. The Occasion Email Attribute Mapping object 375 includes an Occasion Email Attribute Mapping ID 375 for identification, a Metadata Attribute Name 375B to identify specific Metadata objects 346, and an Occasion Communication Setting ID to associate it with the Occasion Communication Setting object 330. As illustrated, the Occasion Email Attribute Mapping object 370 identifies one or more Metadata objects 346 which includes name/value pairs. For example, for a Metadata object 346 associated with visitors, the Field Name 346A may be "Visitor Email Address" and the Field Value 346B may be the visitor's actual email address.

As illustrated, each Visitor object 390 may be associated with one or more Health Verification objects 395 to provide health verification information related to the visitor. Each Health Verification object 395 includes a Health Verification ID 395A for identification, a Visitor ID 390A to uniquely identify the visitor, and an Event Key value 395B provided one the visitor is in compliance with the vaccination and testing requirements for an associated occasion. For example, the Event Key value 395B may be encoded in the QR code once the visitor has provided the requested health information. In some implementations, the visitor's health verification, contained in the Health Verification object 395, may be used across multiple occasions. For example, if the visitor provides health verification information for a particular event (e.g., a proof of vaccination upload), that health verification information may automatically be evaluated and used as a health verification for other occasions (e.g., returning to work).

Note that various other data objects and relationships may be specified within the data model 301 while still complying with the underlying principles of the invention. One significant aspect of this arrangement is that it provides flexibility and scalability, allowing individual changes to be made by an administrator in response to changing health requirements or events, without affecting other portions of the system architecture.

Figure 4:
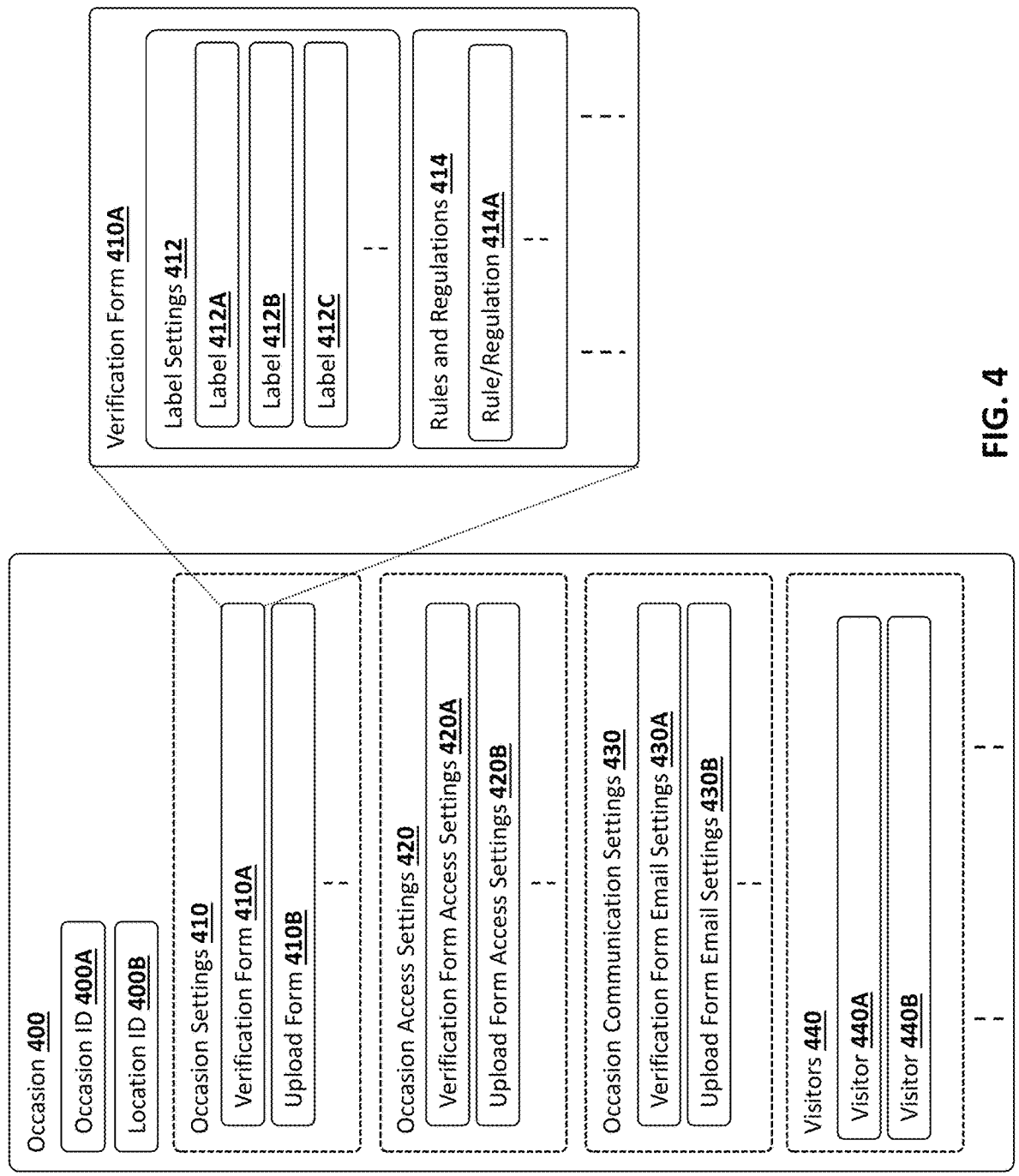
FIG. 4 illustrates an arrangement of graphical user interface (GUI) elements for one or more implementations.

FIG. 4 illustrates an example admin graphical user interface (GUI) 180 arrangement in which the graphical elements for specifying configuration options are arranged based on the relationships between objects in the data model 301. An occasion configuration region 400 provides configurable options for a particular occasion, identified by an Occasion ID field 400A and associated with a location identified by a Location ID field 400B.

The occasion configuration region 400 includes sub-regions for occasion settings 410, occasion access settings 420, occasion communication settings 430, and visitors 440. The administrator 101 uses the occasion settings region 410 for configuring occasion settings, including health verification and upload requirements for attendance. Within the occasion settings region 410 is a verification form element 410A associated with verification requirements for each visitor (e.g., such as the questionnaire described above) and an upload form element 410B associated with the health documentation required for attendance (e.g., such as documentation of vaccination status and/or negative test results). In one embodiment, the verification form element 410A and upload form element 410B include hyperlinks which, when selected by the administrator 101, generate a corresponding window or region to read and enter configuration data. The verification form 410A, which is illustrated as an example, includes label settings 412 comprising a plurality of labels 412A-C and a rules and regulations region 414 comprising one or more rules/regulations 414A. Both the labels 412A-C and rules/regulations 414A drive much of the functionality of the verification form 410A, and are selectable and configurable by the administrator 101 to implement the desired verification requirements for the occasion.

In some implementations, each Rule/Regulation 414A configuration window includes a plurality of selectable options such as a list of acceptable vaccine types (e.g, Pfizer, Moderna, Novavax, etc), health testing types (nucleic acid amplification tests (NAATs), antigen tests, etc), the accepted verification methods (e.g., documentation upload, user verification, etc), and the timing required for health verification prior to the occasion (e.g., within 7 days prior to the event).

The occasion access settings region 420 includes selectable elements 420A-B corresponding to different occasion access settings including verification form access settings 420A and upload form access settings 420B, which may include hyperlinks which, when selected by the administrator 101, generate a corresponding window or region to read and configure access settings. As mentioned, this may include the level of access provided to a visitor upon complying with the verification and upload requirements. For example, a duration of time may be specified, starting from the day/time of the visitor's negative covid test. At the end of this time period, the visitor's access rights may be revoked, unless or until the visitor provides a more recent negative test result. Various other access settings may be selected and/or configured including a start date and end date, specification of access rights to portions of the event, etc.

The occasion communication settings region 430 includes a list of selectable elements 430A-B related to communication settings including verification form email settings 430A and upload form email settings 430B. These selectable elements may include hyperlinks which, when selected by the administrator 101, generate a corresponding window or region to read and configure communication settings for the occasion. For example, the administrator may configure the verification form email settings 430A using a plurality of labels to specify the text portion of the email message, including an explanation of the verification requirements, as well as one or more links to connect the prospective visitor with the HS service 130 for responding to a questionnaire as described above. Similarly, the upload form email settings 430A may be constructed from labels to provide instructions to the prospective visitor regarding testing requirements and one or more links to upload requested documentation (e.g., proof of vaccination, proof of a negative test result, etc).

The visitor region 440 of one implementation includes selectable elements associated with prospective visitors 440A-B (i.e., individuals invited to or otherwise associated with the occasion). The selectable elements 440A-B are hyperlinks or other selectable elements which, when selected by the administrator 101, generate a corresponding window or region to read and enter configuration data associated with the corresponding visitor. As discussed above, in some implementations, the visitor list and associated visitor data is imported from employee records stored on an external system 290 (e.g., employee data from the external system 290 converted to an object format used by some implementations described herein).

Figure 5:
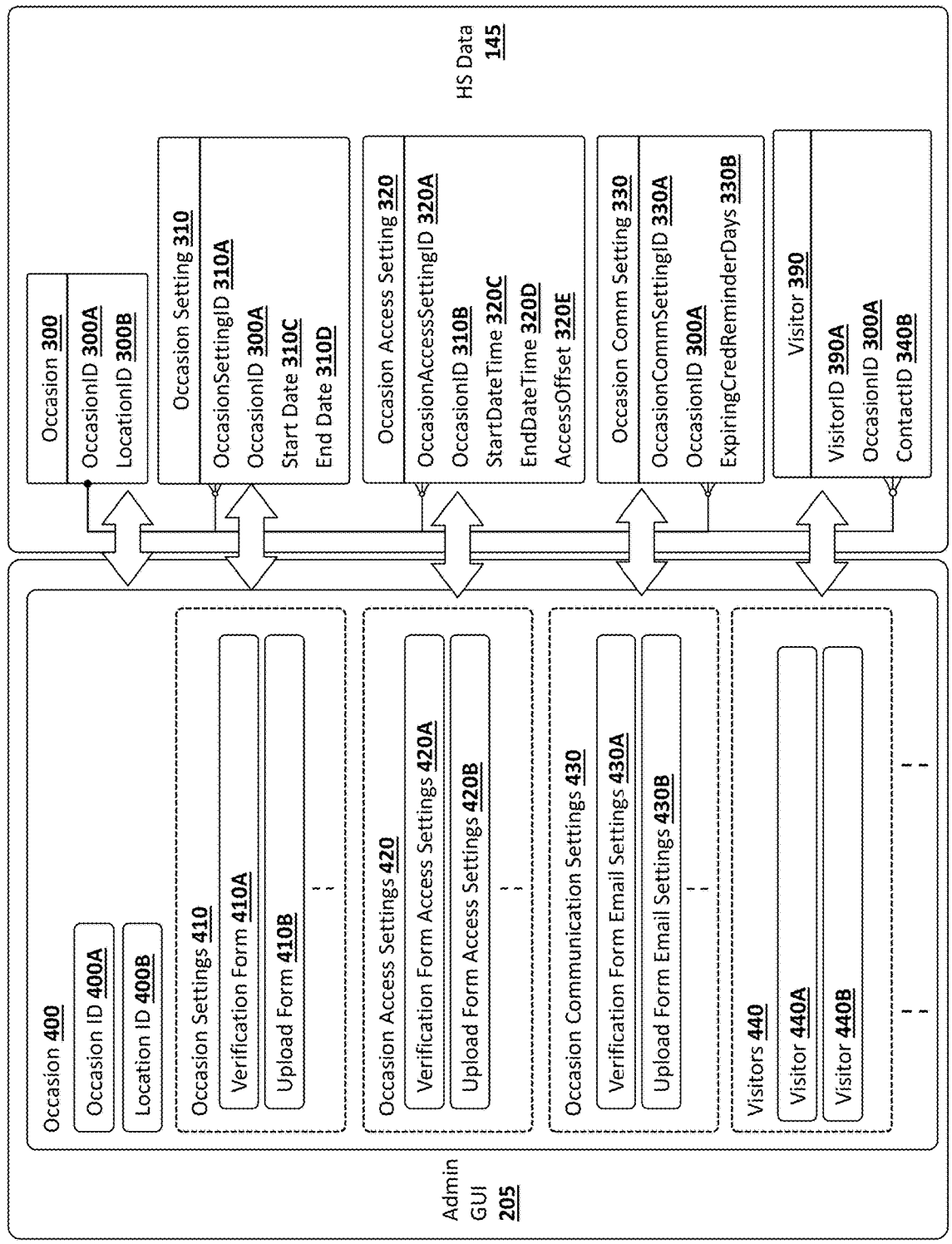
FIG. 5 illustrates a mapping between the GUI elements in FIG. 4 and objects in FIG. 3.

FIG. 5 illustrates how the upper level portions of the admin GUI 180 are mapped to portions of the objects in the data model 301, in accordance with one implementation. In particular, the occasion configuration region 400 maps to the Occasion object 300, the occasion settings region 410 maps to the Occasion Settings object 310, the occasion access settings region 420 maps to the Occasion Access Settings object 320, the occasion communication settings region 430 maps to the Occasion Communication Settings object 330, and the visitors region 440 maps to a set of Visitor objects 390. As the administrator selects elements from within one of the regions, a new window or region corresponding to the selection is generated within the admin GUI 180, which maps to one of the objects associated with the region. For example, selecting the verification form element 410A as shown in FIG. 4, will open a window or region showing details of the verification form, which includes label settings 412 corresponding to the Occasion Label Settings object 340 and rules and regulations 414 corresponding to the Occasion Rules and Regs object 350.

In some implementations, some or all of the data associated with an object is available to the admin GUI 180, based on the selections made within the various regions 410, 420, 430, 440. At least some of this data may be modified by the administrator via the corresponding data fields in the admin GUI 180 and written back to the corresponding object within the HS data 145. Additional examples of an admin GUI 180 are provided below.

Figure 6:
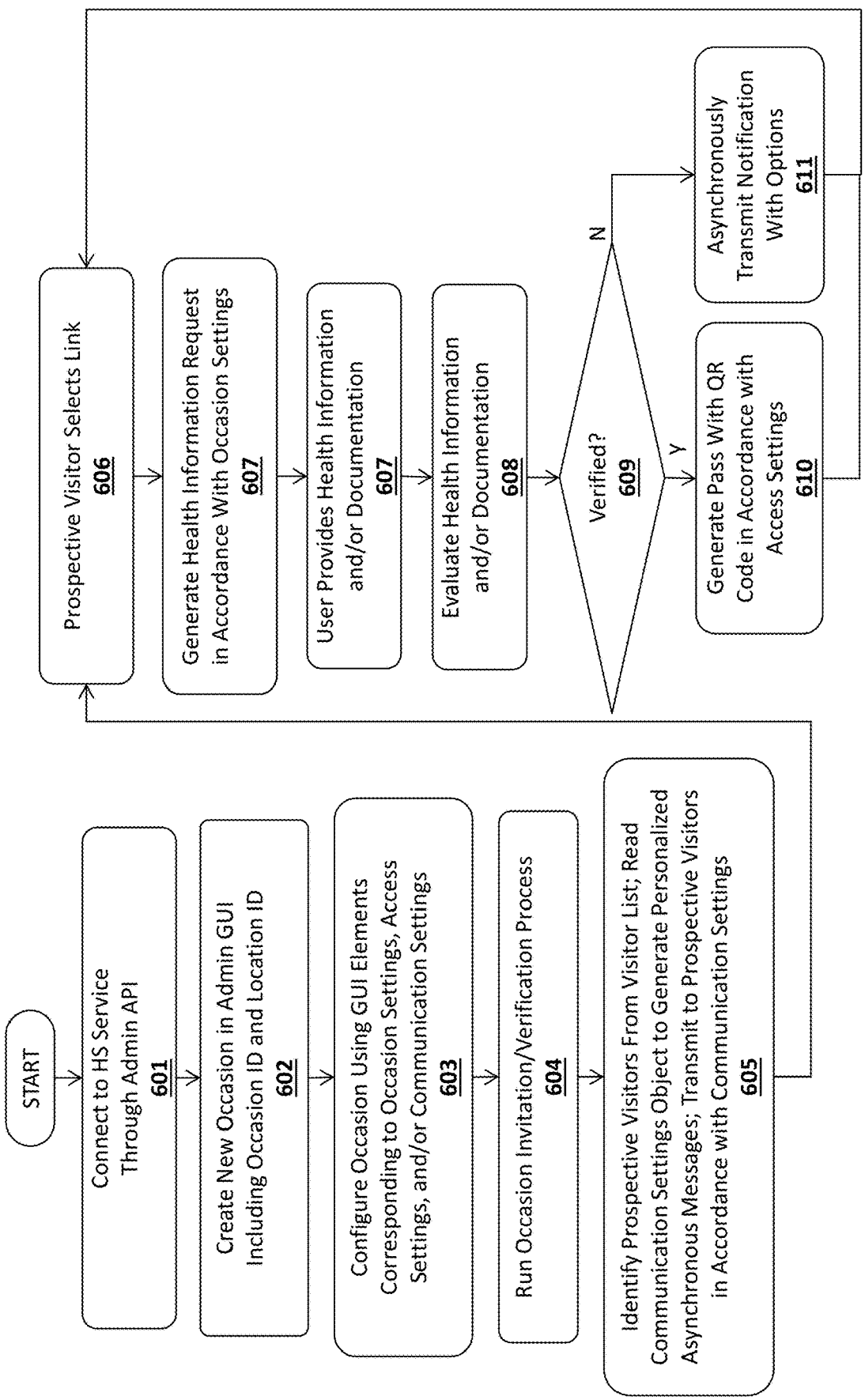
FIG. 6 illustrates a method for configuring and managing health verifications in accordance with at least one implementation.

A method in accordance with one implementation is illustrated in FIG. 6. The method may be implemented on the various architectures described herein, but is not limited to any particular architecture.

At 601, a connection is made to the health and safety (HS) service through an admin API. At 602 a new occasion is created in the Admin GUI with an occasion ID and a location ID. At 603, the occasion is configured using GUI elements corresponding to occasion settings, access settings, and/or communication settings.

At 604, after configuration, the occasion invitation/verification process is run. At 605, prospective visitors are identified from the visitor list and personalized asynchronous messages (e.g., email messages) are generated for the visitors in accordance with the communication settings object. As mentioned, each message may include a link to provide health verification information.

At 606, a prospective visitor selects a corresponding link and, at 607, a health information request is generated in accordance with the occasion settings (e.g., a questionnaire and/or document request). At 608, the health information provided by the prospective visitor is evaluated.

If the health information is verified, determined at 609, then a pass is generated including a QR code in accordance with access settings at 610. If the health information is not verified, then at 611, a new asynchronous message is transmitted to the prospective visitor providing options (e.g., reasons for the failed verification and/or requests for additional information).

Additional features and implementations of the Admin GUI 108 are illustrated in FIGS. 7A-H.

Figure 7A:
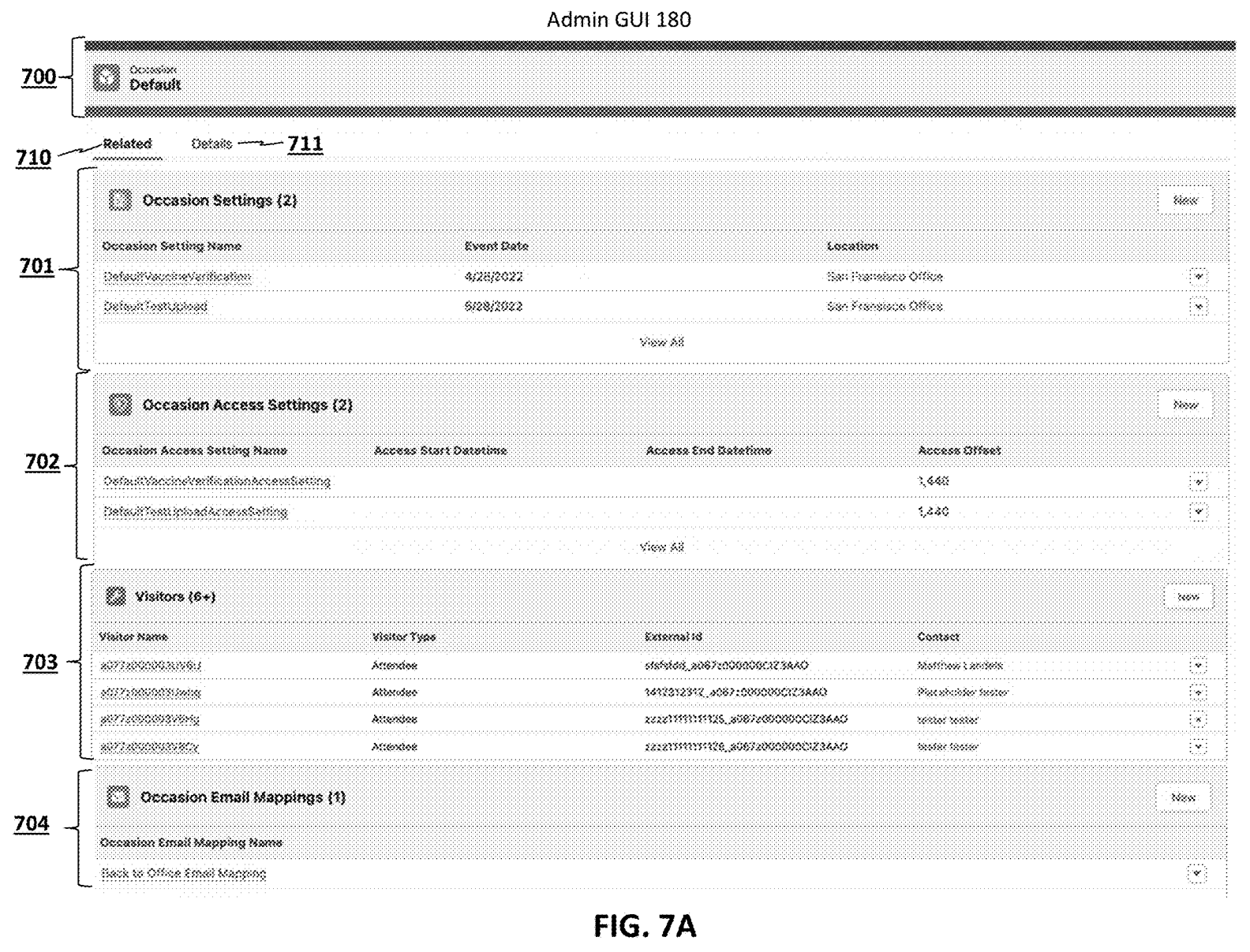
Figure 7B:
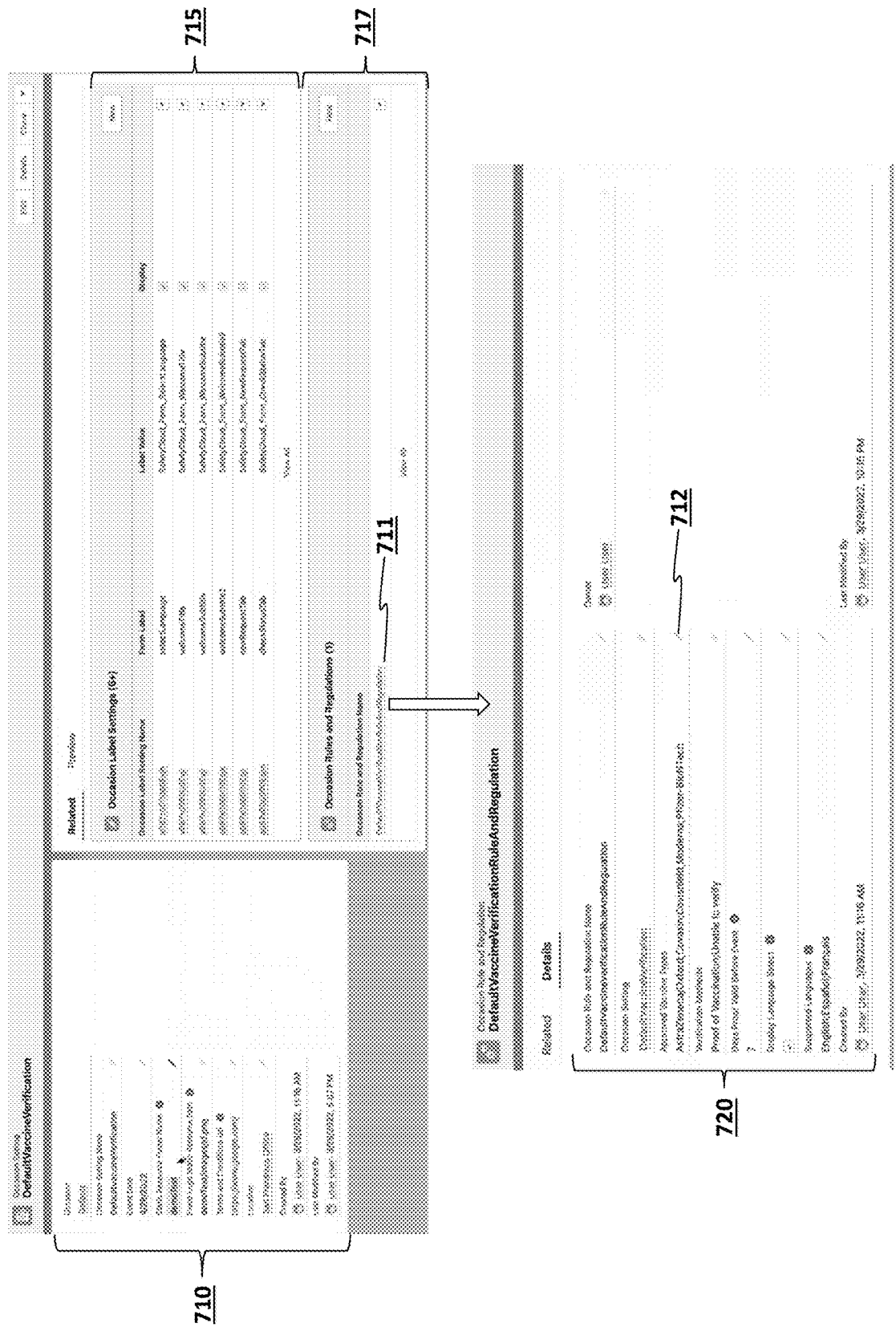

FIG. 7A illustrates an occasion configuration region/window for a selected occasion 700, with a first tab 710 selected to show configuration settings for related objects, including an occasion settings region 701, an occasion access settings region 702, a visitors region 703, and an occasion email mappings region 704. Within each of the interface regions are selectable elements which, when selected, cause a new configuration page to be displayed, allowing configuration options to be specified for the associated object and/or subsystem. For example, selecting DefaultVaccineVerification within the Occasion Settings region/window 701 generates a new page such as shown in FIG. 7B, for configuring variables related to the default vaccine verification occasion settings. Some variables can be entered directly, within region 710, while others can be accessed via additional selectable elements within sub-regions for occasion label settings 715 and occasion rules and regulations 717. As mentioned, labels listed within the label settings can be selected and modified to provide verbiage and/or links to collect health information from prospective visitors. Each rules and regulations object specifies one of the health verification requirements associated with the occasion setting. Selecting the one rules and regulations element 711 in FIG. 7B generates a new data entry window 720 in which the health verification requirements can be viewed/modified, and additional configuration options can be accessed by selecting the edit graphic 712 associated with a corresponding field. For example, the approved vaccine types, verification methods, and the number of days before the event that the verification must be administered can all be edited or added.

Figure 7C:
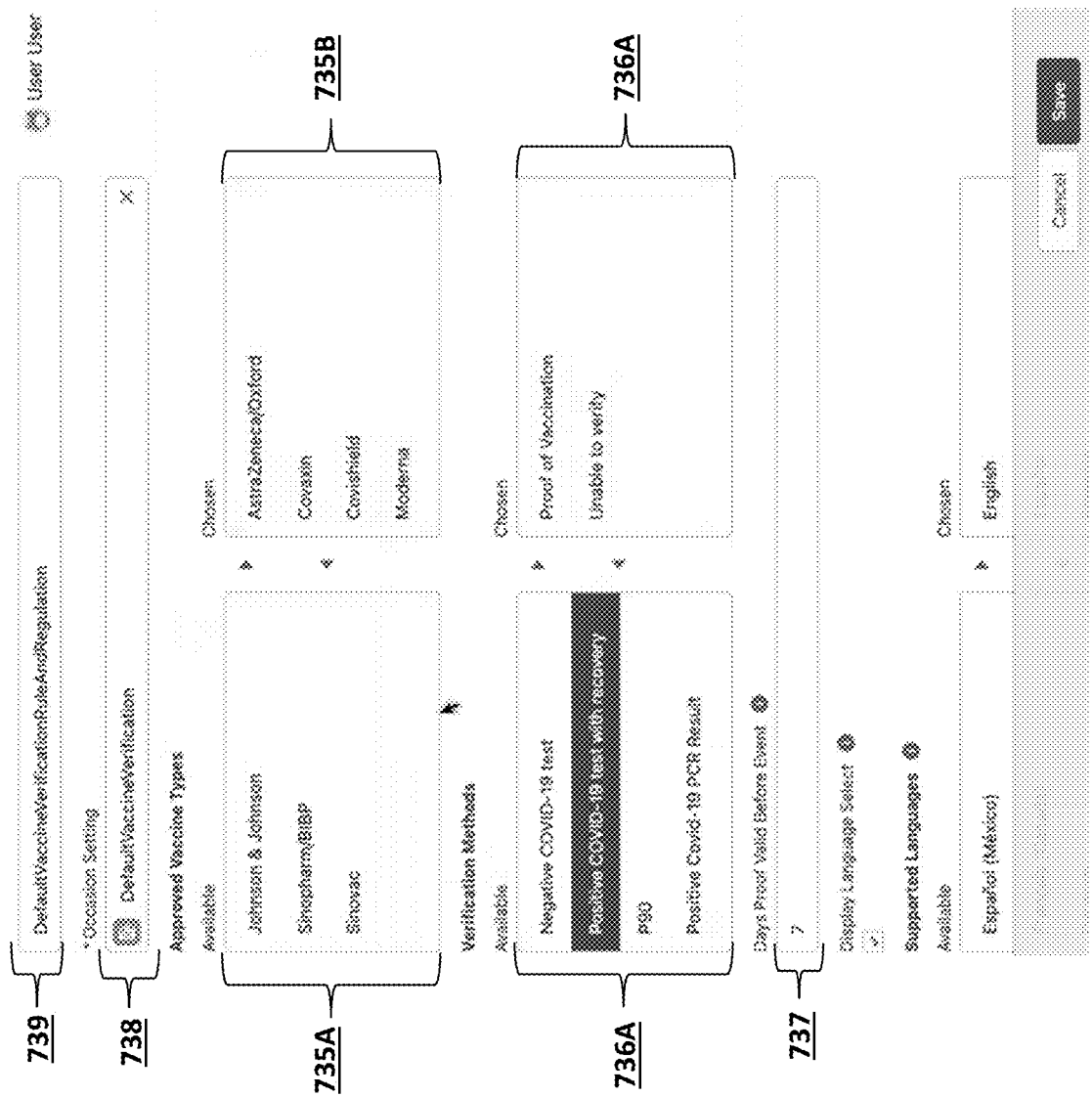

FIG. 7C illustrates a configuration window for configuring settings associated with the default vaccine rule and regulation, identified in field 739. The corresponding occasion setting is indicated in field 738. Two lists of vaccine types are provided: list 735B shows vaccine types which are approved and list 735A shows vaccine types which are not approved. Vaccine types may be moved from list 735A to list 735B to approve the vaccine type under the rule and regulation. Similarly, vaccine types may be moved from list 735B to list 735A to remove the approval of the vaccine type.

Two lists of verification methods are provided: list 736A shows those verification methods which have been chosen for this particular rule and regulation and list 736A shows those verification methods which have not been chosen. Verification methods may be moved from list 736A to list 736B to approve the verification method under the rule and regulation. Similarly, verification methods may be moved from list 735B to list 735A to remove the verification method from the rule and regulation configuration.

A data entry field 737 is provided to set the minimum number of days prior to the event that the vaccine can be administered. Once configuration changes are made to the default vaccine verification rule and regulation, a save button will store the results within the corresponding objects in the data model (e.g., Occasion Rules and Regs object 350).

Figure 7D:
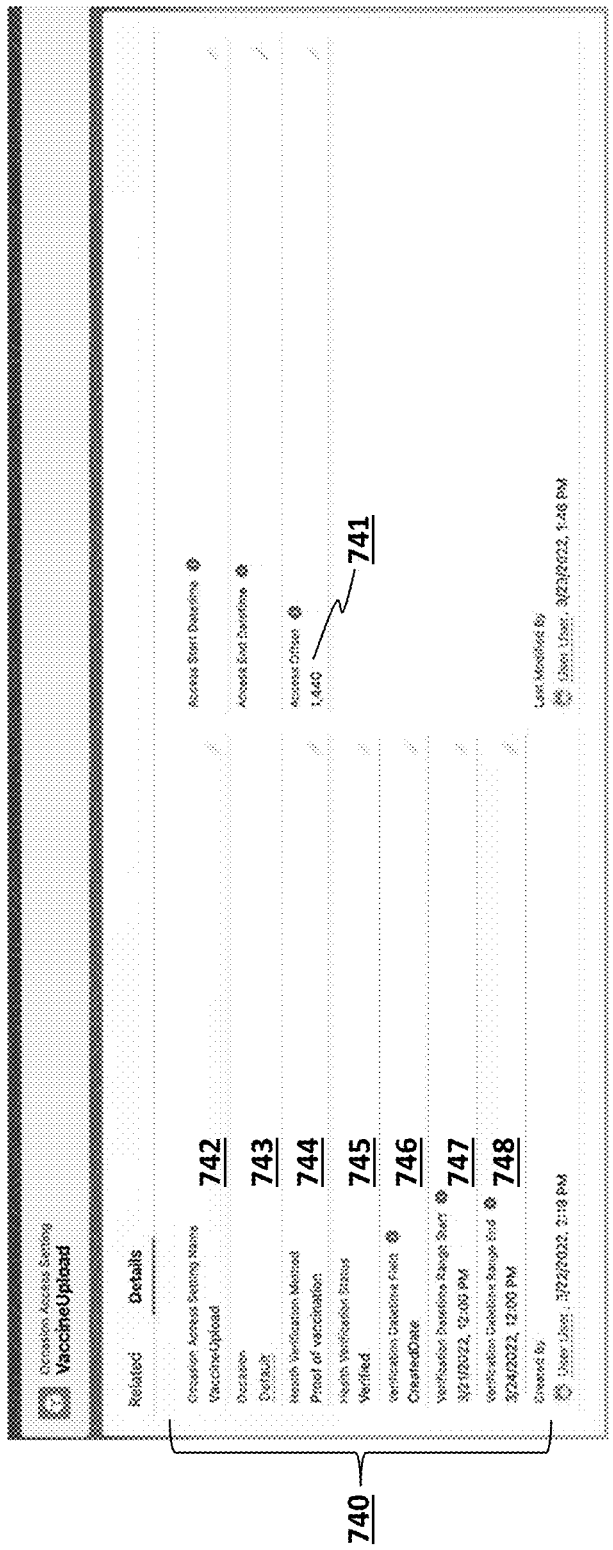

FIG. 7D illustrates an example window showing configuration options 740 for occasion access settings. An access offset value 741 can be set to specify the length of time for which a verification is operable, after which the visitor may be required to resubmit a new verification. In this example, the access offset value 741 is shown in minutes (1440 minutes or 1 day). Also shown is are fields for the access setting name 742, the associated occasion 743, the health verification method that was used 744, the health verification status 745, and date/time fields 746-748 for specifying the date of the verification and the range within which the verification is accepted—which may be used in place of or in combination with the access offset 741.

Figure 7E:
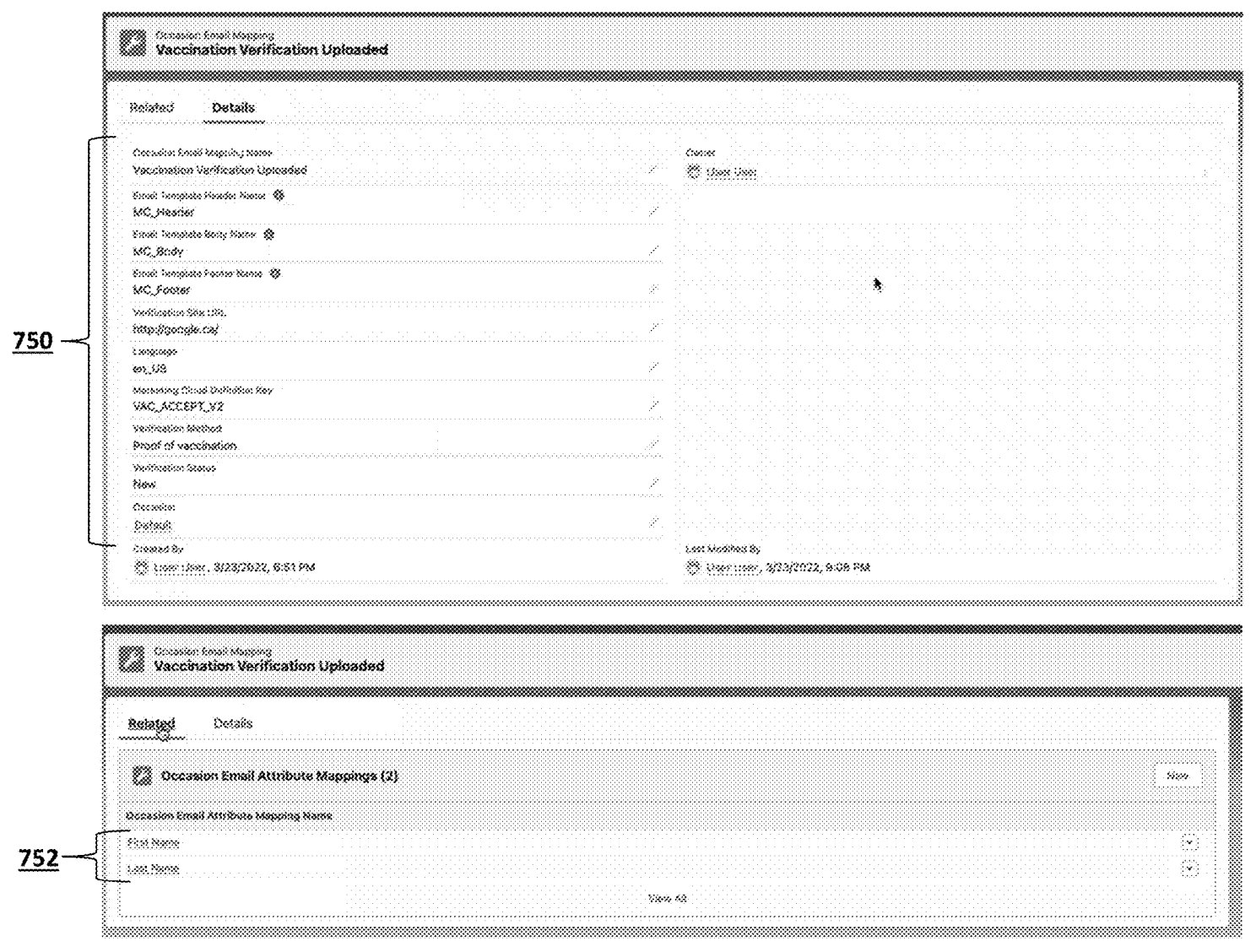

FIG. 7E illustrates an example configuration window for specifying occasion email settings within a set of data entry fields 750 under the Details tab of the window. These include fields for the occasion email mapping name, and template names for identifying the correct email message header, body and footer, each of which may include text, graphics, and/or links. In one implementation, the header, body, and footer comprise separate files or chunks of HTML content which is transmitted to the occasion communication subsystem along with the necessary visitor data for constructing the email message sequences described herein.

The lower portion of FIG. 7E shows an example of occasion email attribute mappings when the Related tab is selected from the occasion email mapping window. Here, the occasion email attribute mappings include the first and last name 752 of each visitor, and may include other information such as the visitors' email addresses or phone numbers.

Figure 7F:
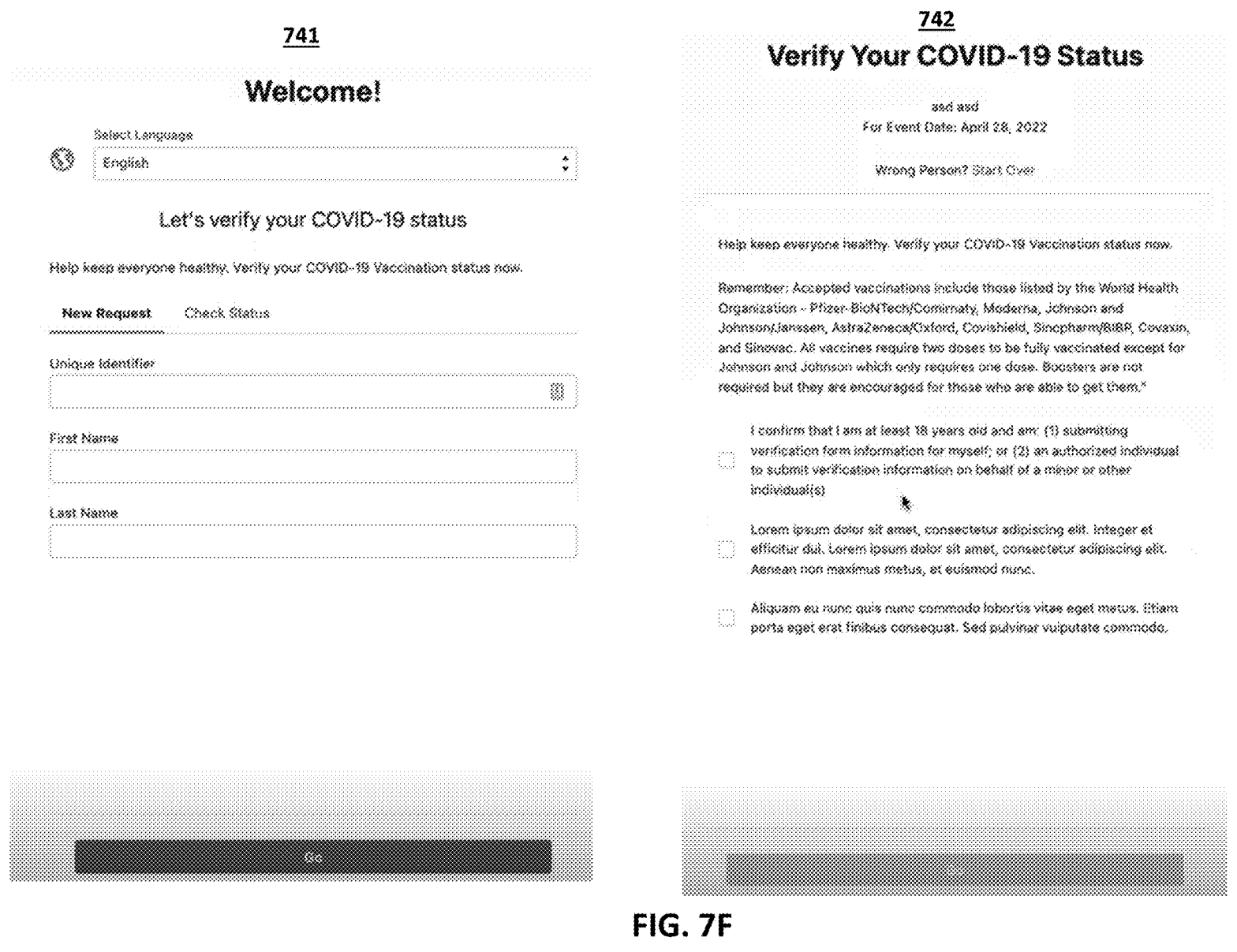

FIG. 7F illustrates an implementation of an email message dynamically generated by/for the occasion communication subsystem 173 based on the occasion settings and occasion communication settings. The first window 741 includes a welcome message and verbiage explaining the purpose of the email. A selection menu is provided to select a language, a field to enter a unique identifier (e.g., a visitor's SSN or employee ID), and fields to enter the prospective visitor's first and last name. Upon entering the requested information and selecting the Go button, a questionnaire window 742 is provided in which the prospective visitor is asked a series of questions related to health. Check boxes are provided in this implementation to confirm each of the corresponding statements.

Figure 7G:
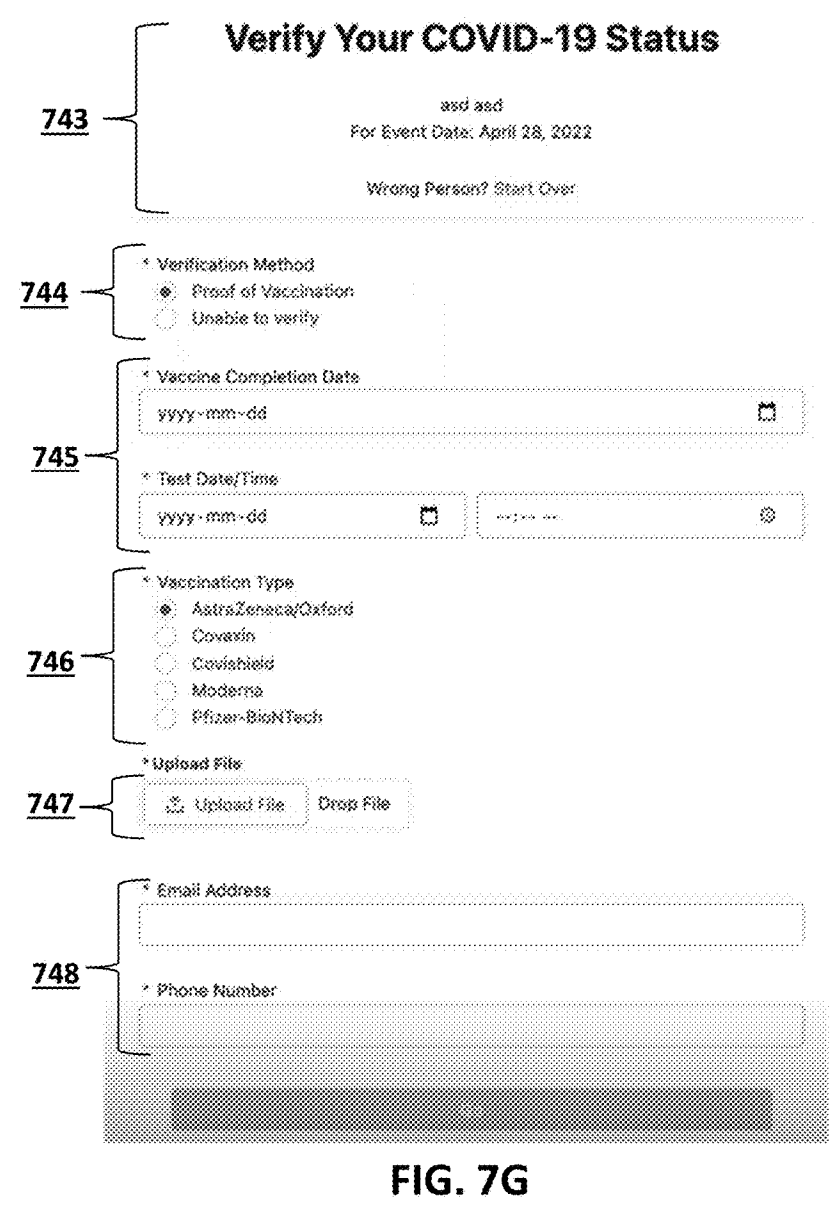

Once the selections on the questionnaire are complete and Go is selected, a health verification page is provided as shown in FIG. 7G. Region 743 describes the purpose of the email. In region 744, the prospective visitor is provided options for the verification method. In this case, there are two options: proof of vaccination and unable to verify. Other options may include a recent test or proof of contraction of the virus followed by a period of recovery.

Fields in region 745 allow the prospective visitor to enter a vaccine completion date and dates of a recent test. Region 746 provides selectable options for a vaccine type and an upload button 747 generates a file system window for the prospective visitor to identify a file containing documentation of the vaccine. Region 748 includes fields for entering the prospective visitor's email address and phone number.

As mentioned, all of the selection options, data fields, informative text, and personalization is dynamically generated based on the occasion settings and/or occasion communication settings associated with this round of messages. Modifications can easily be made via the admin GUI 180—e.g., selecting Default Vaccine Verification from the occasion settings window 701, then selecting the corresponding rules and regulations object 711 (FIG. 7B) to generate a new data entry window 720 in which the health verification requirements can be viewed/modified, and additional configuration options can be accessed by selecting the edit graphic 712 associated with a corresponding field. For example, the approved vaccine types, verification methods, and the number of days before the event that the verification must be administered can all be edited or added.

Example Electronic Devices and Environments

Electronic Device and Machine-Readable Media

One or more parts of the above implementations may include software. Software is a general term whose meaning can range from part of the code and/or metadata of a single computer program to the entirety of multiple programs. A computer program (also referred to as a program) comprises code and optionally data. Code (sometimes referred to as computer program code or program code) comprises software instructions (also referred to as instructions). Instructions may be executed by hardware to perform operations. Executing software includes executing code, which includes executing instructions. The execution of a program to perform a task involves executing some or all of the instructions in that program.

An electronic device (also referred to as a device, computing device, computer, etc.) includes hardware and software. For example, an electronic device may include a set of one or more processors coupled to one or more machine-readable storage media (e.g., non-volatile memory such as magnetic disks, optical disks, read only memory (ROM), Flash memory, phase change memory, solid state drives (SSDs)) to store code and optionally data. For instance, an electronic device may include non-volatile memory (with slower read/write times) and volatile memory (e.g., dynamic random-access memory (DRAM), static random-access memory (SRAM)). Non-volatile memory persists code/data even when the electronic device is turned off or when power is otherwise removed, and the electronic device copies that part of the code that is to be executed by the set of processors of that electronic device from the non-volatile memory into the volatile memory of that electronic device during operation because volatile memory typically has faster read/write times. As another example, an electronic device may include a non-volatile memory (e.g., phase change memory) that persists code/data when the electronic device has power removed, and that has sufficiently fast read/write times such that, rather than copying the part of the code to be executed into volatile memory, the code/data may be provided directly to the set of processors (e.g., loaded into a cache of the set of processors). In other words, this non-volatile memory operates as both long term storage and main memory, and thus the electronic device may have no or only a small amount of volatile memory for main memory.

In addition to storing code and/or data on machine-readable storage media, typical electronic devices can transmit and/or receive code and/or data over one or more machine-readable transmission media (also called a carrier) (e.g., electrical, optical, radio, acoustical or other forms of propagated signals—such as carrier waves, and/or infrared signals). For instance, typical electronic devices also include a set of one or more physical network interface(s) to establish network connections (to transmit and/or receive code and/or data using propagated signals) with other electronic devices. Thus, an electronic device may store and transmit (internally and/or with other electronic devices over a network) code and/or data with one or more machine-readable media (also referred to as computer-readable media).

Software instructions (also referred to as instructions) are capable of causing (also referred to as operable to cause and configurable to cause) a set of processors to perform operations when the instructions are executed by the set of processors. The phrase "capable of causing" (and synonyms mentioned above) includes various scenarios (or combinations thereof), such as instructions that are always executed versus instructions that may be executed. For example, instructions may be executed: 1) only in certain situations when the larger program is executed (e.g., a condition is fulfilled in the larger program; an event occurs such as a software or hardware interrupt, user input (e.g., a keystroke, a mouse-click, a voice command); a message is published, etc.); or 2) when the instructions are called by another program or part thereof (whether or not executed in the same or a different process, thread, lightweight thread, etc.). These scenarios may or may not require that a larger program, of which the instructions are a part, be currently configured to use those instructions (e.g., may or may not require that a user enables a feature, the feature or instructions be unlocked or enabled, the larger program is configured using data and the program's inherent functionality, etc.). As shown by these exemplary scenarios, "capable of causing" (and synonyms mentioned above) does not require "causing" but the mere capability to cause. While the term "instructions" may be used to refer to the instructions that when executed cause the performance of the operations described herein, the term may or may not also refer to other instructions that a program may include. Thus, instructions, code, program, and software are capable of causing operations when executed, whether the operations are always performed or sometimes performed (e.g., in the scenarios described previously). The phrase "the instructions when executed" refers to at least the instructions that when executed cause the performance of the operations described herein but may or may not refer to the execution of the other instructions.

Electronic devices are designed for and/or used for a variety of purposes, and different terms may reflect those purposes (e.g., user devices, network devices). Some user devices are designed to mainly be operated as servers (sometimes referred to as server devices), while others are designed to mainly be operated as clients (sometimes referred to as client devices, client computing devices, client computers, or end user devices; examples of which include desktops, workstations, laptops, personal digital assistants, smartphones, wearables, augmented reality (AR) devices, virtual reality (VR) devices, mixed reality (MR) devices, etc.). The software executed to operate a user device (typically a server device) as a server may be referred to as server software or server code), while the software executed to operate a user device (typically a client device) as a client may be referred to as client software or client code. A server provides one or more services (also referred to as serves) to one or more clients.

The term "user" refers to an entity (e.g., an individual person) that uses an electronic device. Software and/or services may use credentials to distinguish different accounts associated with the same and/or different users. Users can have one or more roles, such as administrator, programmer/developer, and end user roles. As an administrator, a user typically uses electronic devices to administer them for other users, and thus an administrator often works directly and/or indirectly with server devices and client devices.

Figure 8B:
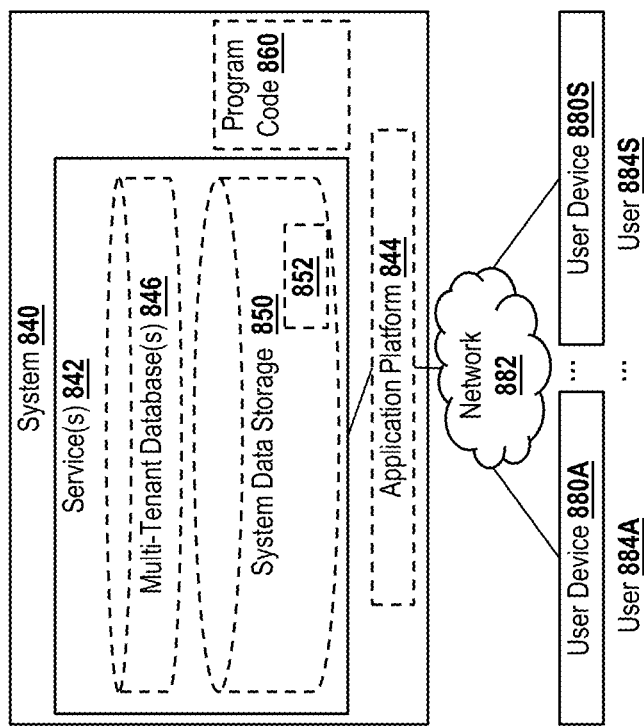
FIG. 8B is a block diagram of a deployment environment according to some example implementations.
Figure 8A:
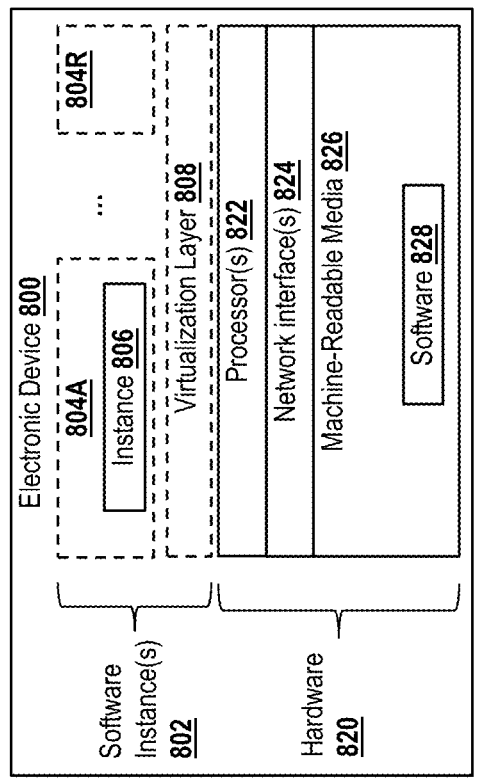
FIG. 8A is a block diagram illustrating an electronic device 1300 according to some example implementations.

FIG. 8A is a block diagram illustrating an electronic device 800 according to some example implementations. FIG. 8A includes hardware 820 comprising a set of one or more processor(s) 822, a set of one or more network interfaces 824 (wireless and/or wired), and machine-readable media 826 having stored therein software 828 (which includes instructions executable by the set of one or more processor(s) 822). The machine-readable media 826 may include non-transitory and/or transitory machine-readable media. Each of the previously described systems, subsystems, and related components such as the HS service 130, data service 140, authentication service 250, asynchronous notification service 160, data field extraction logic 260, and all of the associated APIs 210-211, 252, 270 may be implemented in one or more electronic devices 800. In one implementation: 1) each of the clients is implemented in a separate one of the electronic devices 800 (e.g., in end user devices where the software 828 represents the software to implement clients including the admin 101 and prospective visitors 102 to interface directly and/or indirectly with the HS service 130 (e.g., software 828 represents a web browser, a native client, a portal, a command-line interface, and/or an application programming interface (API) based upon protocols such as Simple Object Access Protocol (SOAP), Representational State Transfer (REST), etc.)); 2) the HS service 130 are implemented in a separate set of one or more of the electronic devices 800 (e.g., a set of one or more server devices where the software 828 represents the software to implement the HS service 130); and 3) in operation, the electronic devices implementing the clients (e.g., such as REST endpoints) and the HS service 130 would be communicatively coupled (e.g., by a network) and would establish between them (or through one or more other layers and/or or other services) connections for submitting configuration data related to an occasion to the HS service 130 (e.g., via serialized object graph requests or other mechanisms) and returning responses to the clients (e.g., serialized object graph responses or other mechanisms). Other configurations of electronic devices may be used in other implementations (e.g., an implementation in which the client and the HS service 130 are implemented on a single one of electronic device 800).

During operation, an instance of the software 828 (illustrated as instance 806 and referred to as a software instance; and in the more specific case of an application, as an application instance) is executed. In electronic devices that use compute virtualization, the set of one or more processor(s) 822 typically execute software to instantiate a virtualization layer 808 and one or more software container(s) 804A-804R (e.g., with operating system-level virtualization, the virtualization layer 808 may represent a container engine (such as Docker Engine by Docker, Inc. or rkt in Container Linux by Red Hat, Inc.) running on top of (or integrated into) an operating system, and it allows for the creation of multiple software containers 804A-804R (representing separate user space instances and also called virtualization engines, virtual private servers, or jails) that may each be used to execute a set of one or more applications; with full virtualization, the virtualization layer 808 represents a hypervisor (sometimes referred to as a virtual machine monitor (VMM)) or a hypervisor executing on top of a host operating system, and the software containers 804A-804R each represent a tightly isolated form of a software container called a virtual machine that is run by the hypervisor and may include a guest operating system; with para-virtualization, an operating system and/or application running with a virtual machine may be aware of the presence of virtualization for optimization purposes). Again, in electronic devices where compute virtualization is used, during operation, an instance of the software 828 is executed within the software container 804A on the virtualization layer 808. In electronic devices where compute virtualization is not used, the instance 806 on top of a host operating system is executed on the "bare metal" electronic device 800. The instantiation of the instance 806, as well as the virtualization layer 808 and software containers 804A-804R if implemented, are collectively referred to as software instance(s) 802.

Alternative implementations of an electronic device may have numerous variations from that described above. For example, customized hardware and/or accelerators might also be used in an electronic device.

Example Environment

FIG. 8B is a block diagram of a deployment environment according to some example implementations. A system 840 includes hardware (e.g., a set of one or more server devices) and software to provide service(s) 842, including the HS service 130. In some implementations the system 840 is in one or more datacenter(s). These datacenter(s) may be: 1) first party datacenter(s), which are datacenter(s) owned and/or operated by the same entity that provides and/or operates some or all of the software that provides the service(s) 842; and/or 2) third-party datacenter(s), which are datacenter(s) owned and/or operated by one or more different entities than the entity that provides the service(s) 842 (e.g., the different entities may host some or all of the software provided and/or operated by the entity that provides the service(s) 842). For example, third-party datacenters may be owned and/or operated by entities providing public cloud services (e.g., Amazon.com, Inc. (Amazon Web Services), Google LLC (Google Cloud Platform), Microsoft Corporation (Azure)).

The system 840 is coupled to user devices 880A-880S over a network 882. The service(s) 842 may be on-demand services that are made available to one or more of the users 884A-884S working for one or more entities other than the entity which owns and/or operates the on-demand services (those users sometimes referred to as outside users) so that those entities need not be concerned with building and/or maintaining a system, but instead may make use of the service(s) 842 when needed (e.g., when needed by the users 884A-884S). The service(s) 842 may communicate with each other and/or with one or more of the user devices 880A-880S via one or more APIs (e.g., a REST API). In some implementations, the user devices 880A-880S are operated by users 884A-884S, and each may be operated as a client device and/or a server device. In some implementations, one or more of the user devices 880A-880S are separate ones of the electronic device 800 or include one or more features of the electronic device 800.

In some implementations, the system 840 is a multi-tenant system (also known as a multi-tenant architecture). The term multi-tenant system refers to a system in which various elements of hardware and/or software of the system may be shared by one or more tenants. A multi-tenant system may be operated by a first entity (sometimes referred to a multi-tenant system provider, operator, or vendor; or simply a provider, operator, or vendor) that provides one or more services to the tenants (in which case the tenants are customers of the operator and sometimes referred to as operator customers). A tenant includes a group of users who share a common access with specific privileges. The tenants may be different entities (e.g., different companies, different departments/divisions of a company, and/or other types of entities), and some or all of these entities may be vendors that sell or otherwise provide products and/or services to their customers (sometimes referred to as tenant customers). A multi-tenant system may allow each tenant to input tenant specific data for user management, tenant-specific functionality, configuration, customizations, non-functional properties, associated applications, etc. A tenant may have one or more roles relative to a system and/or service. For example, in the context of a customer relationship management (CRM) system or service, a tenant may be a vendor using the CRM system or service to manage information the tenant has regarding one or more customers of the vendor. As another example, in the context of Data as a Service (DAAS), one set of tenants may be vendors providing data and another set of tenants may be customers of different ones or all of the vendors' data. As another example, in the context of Platform as a Service (PAAS), one set of tenants may be third-party application developers providing applications/services and another set of tenants may be customers of different ones or all of the third-party application developers.

Multi-tenancy can be implemented in different ways. In some implementations, a multi-tenant architecture may include a single software instance (e.g., a single database instance) which is shared by multiple tenants; other implementations may include a single software instance (e.g., database instance) per tenant; yet other implementations may include a mixed model; e.g., a single software instance (e.g., an application instance) per tenant and another software instance (e.g., database instance) shared by multiple tenants.

In one implementation, the system 840 is a multi-tenant cloud computing architecture supporting multiple services, such as one or more of the following types of services: Marketing Cloud; Customer relationship management (CRM); Business process modeling (BPM); Customer support; External data connectivity; Productivity; Database-as-a-Service; Data-as-a-Service (DAAS or DaaS); Platform-as-a-service (PAAS or PaaS); Infrastructure-as-a-Service (IAAS or IaaS) (e.g., virtual machines, servers, and/or storage); Cache-as-a-Service (CaaS); Analytics; Community; Internet-of-Things (IoT); Industry-specific; Artificial intelligence (AI); Application marketplace ("app store"); Data modeling; Security; and Identity and access management (IAM).

For example, system 840 may include an application platform 844 that enables PAAS for creating, managing, and executing one or more applications developed by the provider of the application platform 844, users accessing the system 840 via one or more of user devices 880A-880S, or third-party application developers accessing the system 840 via one or more of user devices 880A-880S.

In some implementations, one or more of the service(s) 842 may use one or more multi-tenant databases 846, as well as system data storage 850 for system data 852 accessible to system 840. In certain implementations, the system 840 includes a set of one or more servers that are running on server electronic devices and that are configured to handle requests for any authorized user associated with any tenant (there is no server affinity for a user and/or tenant to a specific server). The user devices 880A-880S communicate with the server(s) of system 840 to request and update tenant-level data and system-level data hosted by system 840, and in response the system 840 (e.g., one or more servers in system 840) automatically may generate one or more Structured Query Language (SQL) statements (e.g., one or more SQL queries) that are designed to access the desired information from the multi-tenant database(s) 846 and/or system data storage 850.

In some implementations, the service(s) 842 are implemented using virtual applications dynamically created at run time responsive to queries from the user devices 880A-880S and in accordance with metadata, including: 1) metadata that describes constructs (e.g., forms, reports, workflows, user access privileges, business logic) that are common to multiple tenants; and/or 2) metadata that is tenant specific and describes tenant specific constructs (e.g., tables, reports, dashboards, interfaces, etc.) and is stored in a multi-tenant database. To that end, the program code 860 may be a runtime engine that materializes application data from the metadata; that is, there is a clear separation of the compiled runtime engine (also known as the system kernel), tenant data, and the metadata, which makes it possible to independently update the system kernel and tenant-specific applications and schemas, with virtually no risk of one affecting the others. In some implementations, the program code 860 may form at least a portion of the runtime 200, which provides the execution environment for the HS service 130, data service 140, authentication service 250, asynchronous notification service 160, and various related components described above. Further, in one implementation, the application platform 844 includes an application setup mechanism that supports application developers' creation and management of applications, which may be saved as metadata by save routines. Invocations to such applications, including the HS service 130, may be coded using Procedural Language/Structured Object Query Language (PL/SOQL) that provides a programming language style interface. Invocations to applications may be detected by one or more system processes, which manages retrieving application metadata for the tenant making the invocation and executing the metadata as an application in a software container (e.g., a virtual machine).

Network 882 may be any one or any combination of a LAN (local area network), WAN (wide area network), telephone network, wireless network, point-to-point network, star network, token ring network, hub network, or other appropriate configuration. The network may comply with one or more network protocols, including an Institute of Electrical and Electronics Engineers (IEEE) protocol, a 3rd Generation Partnership Project (3GPP) protocol, a 4$^{th}$ generation wireless protocol (4G) (e.g., the Long Term Evolution (LTE) standard, LTE Advanced, LTE Advanced Pro), a fifth generation wireless protocol (5G), and/or similar wired and/or wireless protocols, and may include one or more intermediary devices for routing data between the system 840 and the user devices 880A-880S.

Each user device 880A-880S (such as a desktop personal computer, workstation, laptop, Personal Digital Assistant (PDA), smartphone, smartwatch, wearable device, augmented reality (AR) device, virtual reality (VR) device, etc.) typically includes one or more user interface devices, such as a keyboard, a mouse, a trackball, a touch pad, a touch screen, a pen or the like, video or touch free user interfaces, for interacting with a graphical user interface (GUI) provided on a display (e.g., a monitor screen, a liquid crystal display (LCD), a head-up display, a head-mounted display, etc.) in conjunction with pages, forms, applications and other information provided by system 840. For example, the user interface device can be used to access data and applications hosted by system 840, and to perform searches on stored data, and otherwise allow one or more of users 884A-884S to interact with various GUI pages that may be presented to the one or more of users 884A-884S. User devices 880A-880S might communicate with system 840 using TCP/IP (Transfer Control Protocol and Internet Protocol) and, at a higher network level, use other networking protocols to communicate, such as Hypertext Transfer Protocol (HTTP), File Transfer Protocol (FTP), Andrew File System (AFS), Wireless Application Protocol (WAP), Network File System (NFS), an application program interface (API) based upon protocols such as Simple Object Access Protocol (SOAP), Representational State Transfer (REST), etc. In an example where HTTP is used, one or more user devices 880A-880S might include an HTTP client, commonly referred to as a "browser," for sending and receiving HTTP messages to and from server(s) of system 840, thus allowing users 884A-884S of the user devices 880A-880S to access, process and view information, pages and applications available to it from system 840 over network 882.

CONCLUSION

In the above description, numerous specific details such as resource partitioning/sharing/duplication implementations, types and interrelationships of system components, and logic partitioning/integration choices are set forth in order to provide a more thorough understanding. The invention may be practiced without such specific details, however. In other instances, control structures, logic implementations, opcodes, means to specify operands, and full software instruction sequences have not been shown in detail since those of ordinary skill in the art, with the included descriptions, will be able to implement what is described without undue experimentation.

References in the specification to "one implementation," "an implementation," "an example implementation," etc., indicate that the implementation described may include a particular feature, structure, or characteristic, but every implementation may not necessarily include the particular feature, structure, or characteristic. Moreover, such phrases are not necessarily referring to the same implementation. Further, when a particular feature, structure, and/or characteristic is described in connection with an implementation, one skilled in the art would know to affect such feature, structure, and/or characteristic in connection with other implementations whether or not explicitly described.

For example, the figure(s) illustrating flow diagrams sometimes refer to the figure(s) illustrating block diagrams, and vice versa. Whether or not explicitly described, the alternative implementations discussed with reference to the figure(s) illustrating block diagrams also apply to the implementations discussed with reference to the figure(s) illustrating flow diagrams, and vice versa. At the same time, the scope of this description includes implementations, other than those discussed with reference to the block diagrams, for performing the flow diagrams, and vice versa.

Bracketed text and blocks with dashed borders (e.g., large dashes, small dashes, dot-dash, and dots) may be used herein to illustrate optional operations and/or structures that add additional features to some implementations. However, such notation should not be taken to mean that these are the only options or optional operations, and/or that blocks with solid borders are not optional in certain implementations.

The detailed description and claims may use the term "coupled," along with its derivatives. "Coupled" is used to indicate that two or more elements, which may or may not be in direct physical or electrical contact with each other, co-operate or interact with each other.

While the flow diagrams in the figures show a particular order of operations performed by certain implementations, such order is exemplary and not limiting (e.g., alternative implementations may perform the operations in a different order, combine certain operations, perform certain operations in parallel, overlap performance of certain operations such that they are partially in parallel, etc.).

While the above description includes several example implementations, the invention is not limited to the implementations described and can be practiced with modification and alteration within the spirit and scope of the appended claims.

What is claimed is:

1. A method implemented in a set of one or more electronic devices, the method comprising:
    receiving configuration data in a graphical user interface (GUI) for configuring a plurality of separate subsystems to implement health and safety protocols for an occasion, the separate subsystems including a health verification subsystem to indicate one or more health verification requirements for attending the occasion, an occasion communication subsystem to manage communication with prospective visitors to the occasion, and an occasion access subsystem to generate electronic passes to the occasion for prospective visitors who comply with the health verification requirements;
    storing the configuration data in accordance with a data model/schema comprising a plurality of interrelated objects, each of the separate subsystems associated with at least one object of the plurality of interrelated objects;
    dynamically generating and transmitting, by the occasion communication subsystem, a first set of personalized messages to the prospective visitors requesting health information in accordance with the one or more health verification requirements, each personalized message including a link to direct the corresponding prospective visitor to the health verification subsystem to provide the requested health information;
    evaluating, by the health verification subsystem, health information received from at least some of the prospective visitors and, based on the evaluation;
    identifying, by the health verification subsystem, a first plurality of the prospective visitors in compliance with the health verification requirements and a second plurality of the prospective visitors not in compliance with the health verification requirements; and
    generating, by the occasion access subsystem, personalized electronic passes to the occasion for each of the first plurality of prospective visitors.

2. The method of claim 1, further comprising:
    dynamically generating and transmitting, by the occasion communication subsystem, a second set of personalized messages, each personalized message transmitted to one of the first plurality of prospective visitors and including a personalized electronic pass for a corresponding one of the first plurality of prospective visitors.

3. The method of claim 2, further comprising:
    dynamically generating and transmitting, by the occasion communication subsystem, a third set of personalized messages, each personalized message transmitted to one of the second plurality of prospective visitors and including an indication of one or more reasons why the corresponding prospective visitor has not complied with the health verification requirements for the occasion.

4. The method of claim 1 wherein the plurality of interrelated objects have a hierarchical arrangement which is reproduced, at least in part, within the GUI as a hierarchical arrangement of selectable elements, each selectable element corresponding to at least one of the interrelated objects.

5. The method of claim 1 wherein the one or more health verification requirements comprise responses to a health questionnaire and uploading of health test results and/or vaccination documentation.

6. The method of claim 5 wherein the one or more health verification requirements are configurable via the GUI to indicate one or more types of accepted health tests or vaccination types.

7. The method of claim 1 wherein the personalized electronic passes comprise QR codes generated based on a combination of a visitor identification value and an occasion identification value.

8. The method of claim 1 wherein the first and second sets of personalized messages are email messages generated based on email data specified via the GUI and stored within one or more of the interrelated data objects, the email data comprising header data, body data, and footer data, wherein at least one of the header data or body data are configurable to identify graphical images associated with the occasion and the body data is configurable via one or more labels to provide verbiage indicating a purpose of the email message.

9. The method of claim 1 wherein the data model/schema comprises an occasion object to store configuration data for the occasion, an occasion settings object comprising a child of the occasion object, the occasion settings object to store health verification requirements for the occasion, either directly or within one or more child objects.

10. The method of claim 9 wherein the data schema further comprises an occasion access settings object comprising a child of the occasion object and an occasion communication settings object comprising a child of the occasion object, the occasion access settings object to store configuration data for the occasion access subsystem and the occasion communication settings object to store configuration data for the occasion communication subsystem.

11. The method of claim 1 further comprising:
    extracting prospective visitor data from visitor data records provided from an external system in a first data format; and
    mapping the visitor data into one or more corresponding objects of the plurality of interrelated objects.

12. The method of claim 11 wherein the visitor records are provided from the external system in a JSON stream, the method further comprising:
- parsing the JSON stream to identify and extract the prospective visitor data from data fields of the visitor data records;
- storing the visitor data in an intermediate metadata format; and
- mapping the data fields from the intermediate metadata format into the one or more corresponding objects.

13. A system comprising:
- at least one non-transitory machine-readable storage medium to store software; and
- a set of one or more electronic devices, coupled to the at least one non-transitory machine-readable storage medium, to execute the software configurable to a health and safety service comprising:
  - a graphical user interface (GUI) to receive configuration data to configure a plurality of subsystems to implement health and safety protocols for an occasion, wherein the configuration data is stored in accordance with a data model/schema comprising a plurality of interrelated objects, each of the plurality of subsystems associated with at least one object of the plurality of interrelated objects;
  - a health verification subsystem, which is one of the plurality of subsystems, to identify the occasion and one or more health verification requirements for prospective visitors to the occasion, and to evaluate health information received from at least some of the prospective visitors; and
  - an occasion communication subsystem, which is one of the plurality of subsystems, to manage communication with the prospective visitors, wherein responsive to a first request from the health verification subsystem, the occasion communication subsystem is to dynamically generate and transmit a first set of personalized messages to the prospective visitors requesting health information in accordance with the one or more health verification requirements, each message including a link to direct the corresponding prospective visitor to one or more health information submission pages provided by the health verification subsystem in which to provide the requested health information; and
  - an occasion access subsystem, which is one of the plurality of subsystems, to generate a plurality of electronic passes to the occasion in response to a corresponding plurality of indications from the health verification subsystem that a corresponding plurality of prospective visitors have provided health information in compliance with the health verification requirements.

14. The method of claim 13 wherein the occasion communication subsystem is to transmit a second set of personalized messages to the corresponding plurality of prospective visitors, each message of the second set of personalized messages including a corresponding electronic pass of the plurality of electronic passes.

15. The system of claim 13, the GUI comprising a plurality of selectable elements arranged, at least in part, based on relationships between the subsystems specified in a data model, the selectable elements including a first element associated with the health verification subsystem, a second element associated with the occasion communication subsystem, and a third element associated with the occasion access subsystem, wherein each element of the first, second, and third elements, when selected, is to provide configuration options for independently configuring a corresponding one or the subsystems.

16. The system of claim 15 wherein responsive to selection of the first element, the GUI is to provide one or more additional selectable elements to specify details associated with the one or more health verification requirements for prospective visitors to the occasion.

17. The system of claim 16 wherein the one or more additional selectable elements comprises one or more labels to inform prospective visitors and one or more rules and regulations objects to indicate health verifications required to attend the occasion.

18. The system of claim 17 wherein the health verifications include one or more of: a verification questionnaire, a testing verification, and a vaccination verification.

19. The system of claim 18 wherein the testing verification and/or vaccine verification is to include a link to upload documentation related to testing and/or vaccination of a corresponding prospective visitor.

* * * * *